United States Patent
Albizati et al.

(10) Patent No.: US 7,173,059 B2
(45) Date of Patent: Feb. 6, 2007

(54) INTERMEDIATES USEFUL IN THE SYNTHESIS OF HIV-PROTEASE INHIBITORS AND METHODS FOR PREPARING THE SAME

(75) Inventors: Kim Francis Albizati, San Diego, CA (US); Srinivasan Babu, San Diego, CA (US)

(73) Assignee: Agouron Pharmaceuticals, Inc., San Diego, CA (US)

( * ) Notice: Subject to any disclaimer, the term of this patent is extended or adjusted under 35 U.S.C. 154(b) by 127 days.

(21) Appl. No.: 10/839,111

(22) Filed: May 4, 2004

(65) Prior Publication Data

US 2005/0250949 A1    Nov. 10, 2005

Related U.S. Application Data

(60) Provisional application No. 60/469,235, filed on May 8, 2003.

(51) Int. Cl.
*A61K 31/4015* (2006.01)
*A61K 31/4035* (2006.01)
*A61K 31/27* (2006.01)
*C07D 207/404* (2006.01)
*C07C 321/28* (2006.01)
*C07C 323/20* (2006.01)

(52) U.S. Cl. ............... 514/417; 514/488; 514/425; 514/417; 548/478; 548/547; 560/16

(58) Field of Classification Search .............. 548/478, 548/547; 560/16; 514/417, 488, 425
See application file for complete search history.

(56) References Cited

U.S. PATENT DOCUMENTS

| 5,484,926 A | 1/1996 | Dressman et al. |
| 5,587,481 A | 12/1996 | Allen et al. |
| 5,705,647 A | 1/1998 | Babu et al. |

FOREIGN PATENT DOCUMENTS

| EP | 0 984 000 A | 3/2000 |
| WO | WO 93/07142 | 4/1993 |
| WO | WO 97/11937 | 4/1997 |
| WO | WO 97/11938 | 4/1997 |
| WO | WO 2004099129 A2 * | 11/2004 |

OTHER PUBLICATIONS

Kano, et al. J. Org. Chem., vol. 54(3), 513-515 (1989).*
White, et al., Chemical Communications, (16), pp. 2012-2013 (2003).*
Dobson, et al., Tetrahedron Letters, 40, pp. 3119-3122 (1999).*
Lewanowicz et al., Advanced Materials for Optics and Electronics, vol. 6, pp. 225-232 (1996).*
Leallyn B. Clapp, J. Am. Chem. Soc., 73, pp. 2584-2586 (1951).*
Clapp, et al., J. Am. Chem. Soc., 73, pp. 2121-2124 (1951).*
Kano, et al., J. Amer. Chem. Soc., 54(3) pp. 513-515 (1989).*
Annedi, et al., J. Org. Chem., 68, pp. 1043-1049 (2003).*
Elall, E., et al., "Synthesis Of Thizolidinones From 1,4-Dithiocyanatobut-2-enes And Their Use As Masked 2-Amino-1-Mercaptobut-3-enes," *J. Chem. Soc. Perkin Trans.* 1, 1987, 2729-2736.
Huber, S., et al., "1,3-Butadienyl Thiocyanate In The Diels-Alder Reaction Followed by a [3,3]- Signatropic Shift," *Helvetica Chimica Acta*, 1986, 1898-1915, vol. 69.
Inaba, T., et al., "(1S)-1-[(4R)-2,2-Dimethyl-1,3-dioxolan-4-yl]-2-hydroxyethylammoniun Benzoate, A Versatile Building Block For Chiral 2-Aminoalkanols: Concise synthesis And Application To Nelfinavir, A Potent HIV-Protease Inhibitor," *J. Org. Chem.*, 2000, 1623-1628, No. 65.
Kano, s., et al., "Effect of Polar Solvents On The Rates Of Claisen Rearrangements: Assessment Of Ionic Character," *The Journal Of Organic Chemistry*, 1989, 515-516, vol. 54.
Lavielle, S., et al., "A Total Slynthesis Of Biotin Based On The Stereoselective Alkylation Of Sulfoxides," *Journal Of The American Chemical Society*, 1978, 1558-1563, vol. 100, No. 5.
Rieger, D., et al., "A Concise Formal Synthesis Of The Potent HIV Protease Inhibitor Nelfinavir Mesylate," *J. Org. Chem.*, 1997, 8546-8548, vol. 62.
White, J., et al., "Total Synthesis Of (+)-Kalkitoxin," *Chem. Comm.*, 2003, 2012-2013, No. 16.
Kano, S., et al., "New Diastereoselective Synthesis Of Oxazolidin-2-ones Through Carbon-Carbon Bond Formation On Cyclic Carbamoyloxy Radicals," *The Journal Of Organic Chemistry*, 1989, 513-516, vol. 54, No. 3.
Reetz, et al., "Asymmetric Dihydroxylation of Chiral γ-Amino α, β-Unsaturated Esters: Turning the Mismatched into the Matched Case via Protective Group Tuning," *Tetrahedron Letters*, 1996, 9293-9296, vol. 37, No. 52.

* cited by examiner

*Primary Examiner*—Joseph K. McKane
*Assistant Examiner*—Nyeemah Grazier
(74) *Attorney, Agent, or Firm*—Keith D. Hutchinson; Bryan C. Zielinski

(57) ABSTRACT

Optically active 3-amino-butene and 1,2-dihydroxy-3-amino-butane intermediate compounds, useful in the synthesis of HIV-protease inhibitors and methods of preparing these intermediate compounds are disclosed.

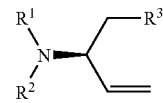

2 Claims, No Drawings

INTERMEDIATES USEFUL IN THE SYNTHESIS OF HIV-PROTEASE INHIBITORS AND METHODS FOR PREPARING THE SAME

This application claims the benefit of U.S. Provisional application Ser. No. 60/469,235, filed May 8, 2003, the contents of which is hereby incorporated by reference in it's entirety.

FIELD OF THE INVENTION

This invention relates generally to 1,2-dihydroxy-3-amino-butanes, their 3-amino-butene precursors and chemical methods for preparing the same. The butene and butane compounds of the invention are useful as intermediates in the synthesis of the protease inhibitor nelfinavir mesylate and its free base, which in turn are useful for the treatment of HIV-infected individuals.

BACKGROUND OF THE INVENTION

Treatment of HIV infected individuals is one of the most pressing biomedical problems of recent times. A promising new therapy has emerged as an important method for preventing or inhibiting the rapid proliferation of the virus in human tissue. HIV protease inhibitors block a key enzymatic pathway in the virus resulting in substantially decreased viral loads, which slows the steady decay of the immune system and its resulting deleterious effects on human health. The HIV protease inhibitor nelfinavir mesylate, having the following formula:

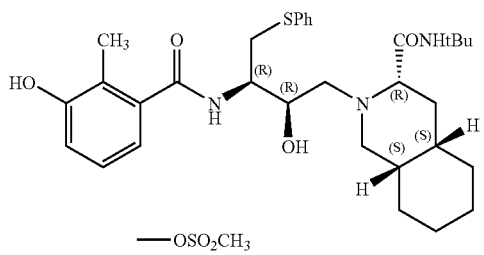

has been shown to be an effective treatment for HIV infected individuals. Nelfinavir mesylate is disclosed in U.S. Pat. No. 5,484,926, which issued Jan. 16, 1996. This patent, in its entirety, is incorporated herein by reference.

Prior to the present invention, the stereochemistry of nelfinavir mesylate products and intermediates prepared by conventional processes was determined by the stereochemistry of the starting materials. Thus, different stereoisomers of nelfinavir mesylate or its free base could only be prepared by the use of specific enantiomeric starting materials. The present invention provides a versatile and useful synthetic route for the preparation of nelfinavir whereby key stereocenters are established at a relatively late stage in the synthesis of the 1,2-dihydroxy-3-amino-butane substituent.

HIV-Protease inhibitors prepared by use of cyclic sulfates are discussed, for example, in U.S. Pat. No. 5,705,647. Asymmetric dihydroxylation, utilized in the present invention to make nelfinavir mesylate intermediates, is discussed generally in WO 93/07142 and in Reetz et al., *Asymmetric Dihydroxylation of Chiral γ-Amino α, β-Unsaturated Esters: Turning the Mismatched into the Matched Case via Protective Group Tuning*, Tetrahedron Letters Vol. 37 9293–9296 (1996).

Other background processes related to the invention are found in U.S. Pat. No. 5,587,481. Processes for producing amide derivatives useful as intermediates in the synthesis of nelfinavir mesylate are found in WO 97/11937 and WO 97/11938. These references are incorporated herein by reference.

SUMMARY OF THE INVENTION

This invention relates to a method for the preparation of an optically active 3-amino-butene, the stereoselective conversion of the optically active 3-amino-butene to an optically active 1,2-dihydroxy-3-amino-butane, and the optically active 3-amino-butene and 1,2-dihydroxy-3-amino-butane produced thereby.

In one embodiment, this invention provides a method for the stereoselective preparation of R,S or R,R amino-hydroxy alkanols by dihydroxylation of the corresponding protected R-amino alkenes. Specifically, this invention provides a 3(R)-amino-butene, a 1,2(R)-dihydroxy-3(R)-amino-butane or a 1,2(S)-dihydroxy-3(R)-amino-butane, a method for the preparation of the 3(R)-amino-butene and a method for the stereoselective dihydroxylation of the protected R-amino butene to form the 1,2(R)-dihydroxy-3(R)-amino-butane or 1,2(S)-dihydroxy-3(R)-amino-butane.

In one of its aspects, the present invention relates to a compound having the formula:

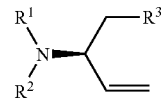

1 wherein $R^1$ is a suitable nitrogen protecting group, $R^2$ is H or $R^1$ together with $R^2$ form a suitable nitrogen protecting group, and $R^3$ is thioalkyl or thioaryl.

In another of its aspects, the present invention relates to compounds according to formula 1, which may be selected from the following group:

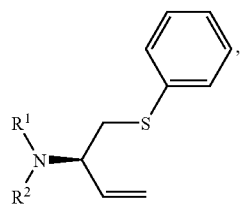

-continued

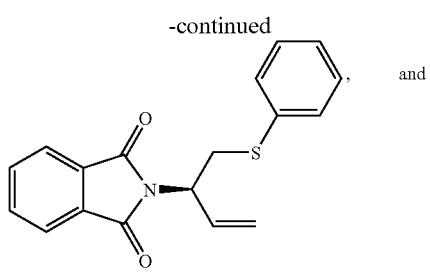
and

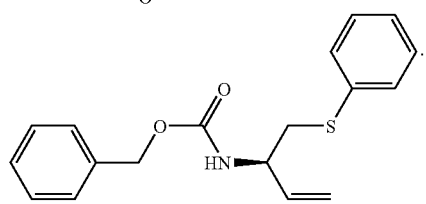

In yet another of its aspects, the present invention relates to a compound having the following formula:

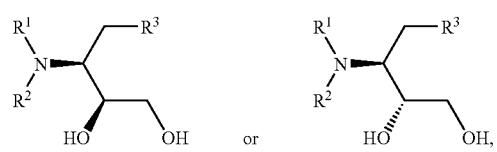

wherein $R^1$ is a suitable nitrogen protecting group and $R^2$ is H or $R^1$ together with $R^2$ form a suitable nitrogen protecting group, and $R^3$ is thioalkyl or thioaryl. Compounds related to formula 2 may include:

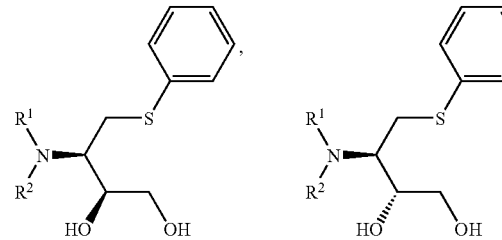

, and

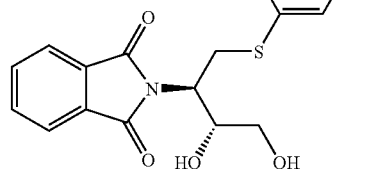

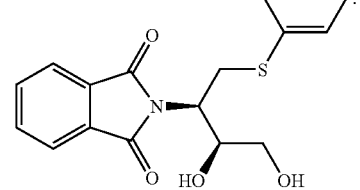

In another aspect, the present invention relates to a compound with the following formula:

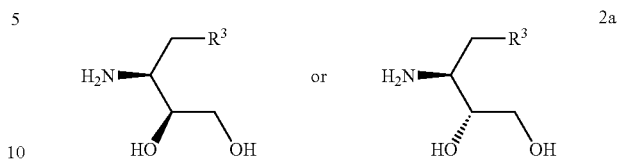

wherein $R^3$ is thioalkyl or thioaryl. Compounds related to formula 2a include:

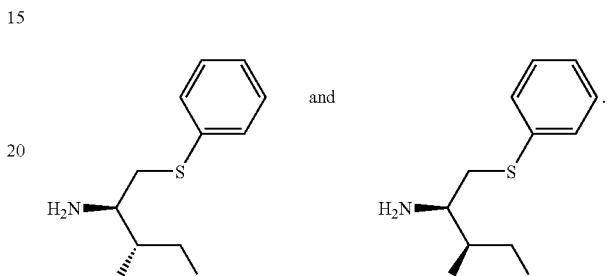

In a further one of its aspects, the present invention relates to a method for the stereoselective preparation of a compound having the formula 4 or 5:

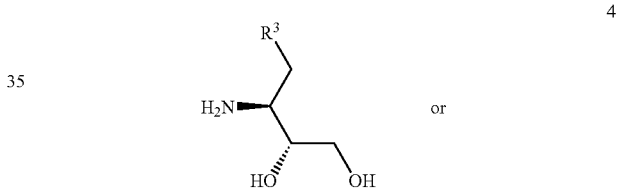

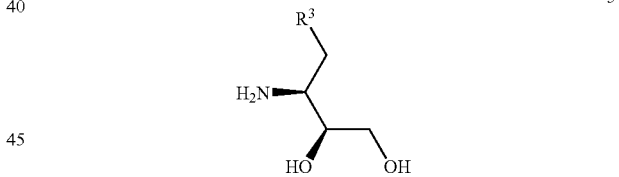

comprising converting a compound of formula 1:

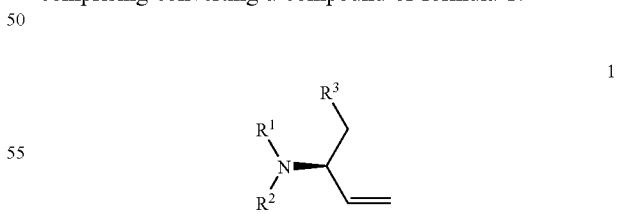

to a compound of formula 4 or formula 5, by treating the respective starting compounds with an osmium-containing oxidizing reagent combination of $K_2OsO_2(OH)_4/K_3Fe(CN)_6$, $K_2CO_3$, $NaHCO_3$ and $CH_3SO_2NH_2$ in the presence of $DHQD_2PHAL$ as a chiral auxiliary reagent to provide the compound represented by formula 4 or 5, respectively, wherein $R^1$ is a suitable nitrogen protecting group and $R^2$ is H or $R^1$ together with $R^2$ form a suitable nitrogen protecting group, and R³ is thioalkyl or thioaryl. Preferably, R³ is an thioaryl group or a thiophenyl group. This present method may further include stereoselectively converting a compound of formula 1 to one of the following compounds:

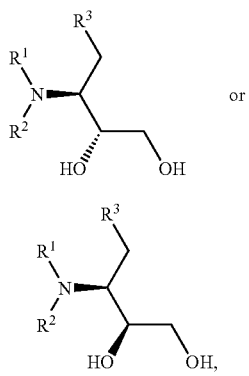

In a further aspect, the invention relates to a method for converting a compound of formula 2 to a compound of formula 4, and/or converting a compound of formula 3 to a compound of formula 5, by removing the nitrogen protection group without inducing racemization to provide the compounds represented by formula 4 or 5, respectively.

In yet a further aspect, the invention relates to a method for converting a compound of formula 6:

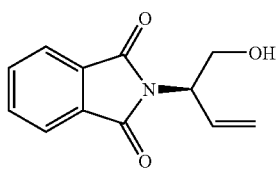

to a compound of formula 7, 7a or formula 8:

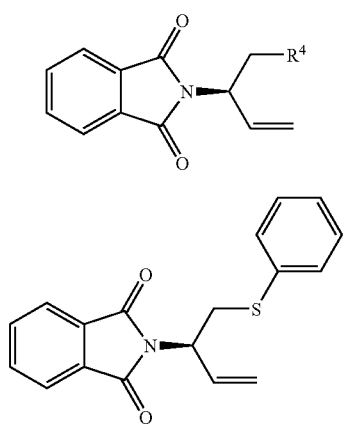

wherein R⁴ in formula 7 is a leaving group, by treating the hydroxy-butene 6 with methane sulfonyl chloride in the presence of a suitable solvent to provide compound 7 or with methane sulfonyl chloride in the presence of an amine base in a polar aprotic solvent to provide butene-mesylate 7a; and

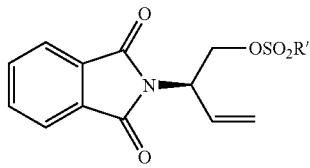

treating butene-mesylate 7a with thiophenoxide, wherein the thiophenoxide is formed in situ using thiophenol and a non-nucleophilic base in a polar aprotic solvent, to provide thiophenyl-butene 8

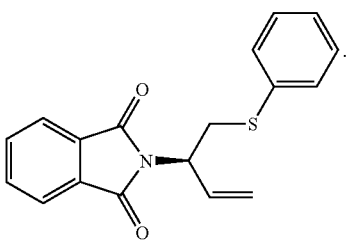

In this reaction, preferably R⁴ is chloro, bromo or —OSO₂—R', wherein R' is alkyl or aryl.

In addition, compound 7a may be stereoselectvely converted to a compound of formula 8, and a compound of formula 8 may be converted to a compound of formulae 9, 10, 11 or 12, respectively:

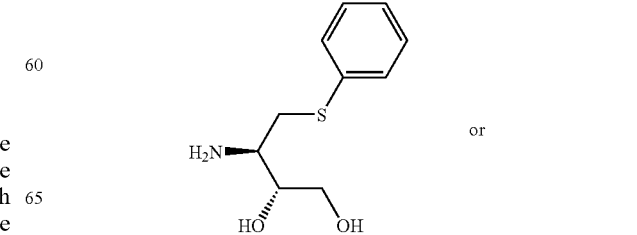

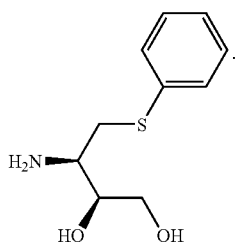

12

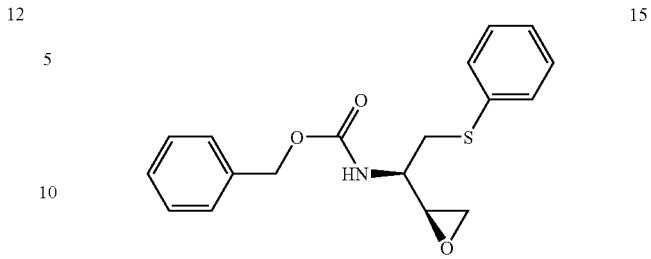

15

In addition, the inventive methods include converting the compound of formula 9 or 10, or a mixture thereof, to a compound of formula 11 or 12 or a mixture thereof by deprotecting the amine. The compounds of formulae 9, 10, 11 or 12 may then be converted to the nelfinavir free base compound, formula 17:

by treating compound of formula 14 with methylphenyl sulfonyl chloride and an amine base solvent followed by treatment with an aqueous base to yield the compound of formula 15.

A compound of formula 15 may be further converted to a compound of formula 16:

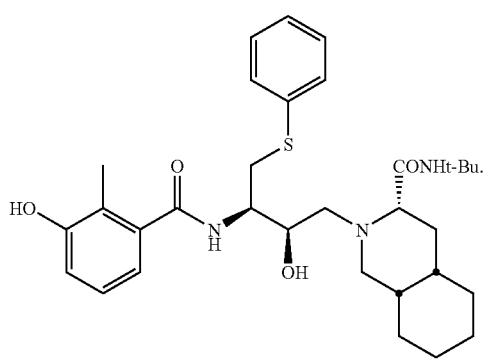

17

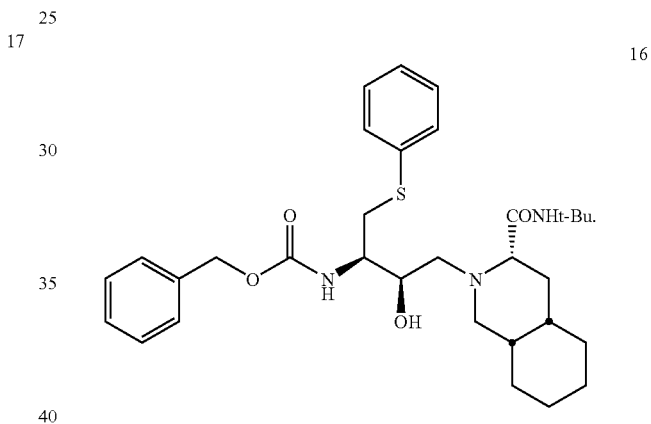

16

A compound of formula 16 may be further converted to nelfinavir free base, formula 17.

In another of its aspects, the present invention relates to a method for converting a compound of formula 8 to a compound of formula 19 or 20:

In a further one of its aspects, the present invention relates to a method for converting a compound of formula 9 to a compound of formula 11 by deprotecting the amine, and then converting a compound of formula 11 to a compound of formula 14:

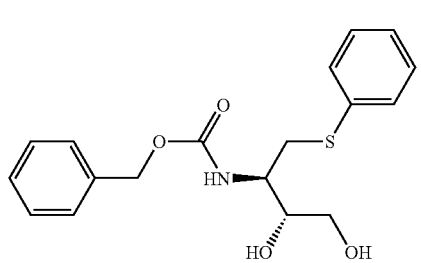

14

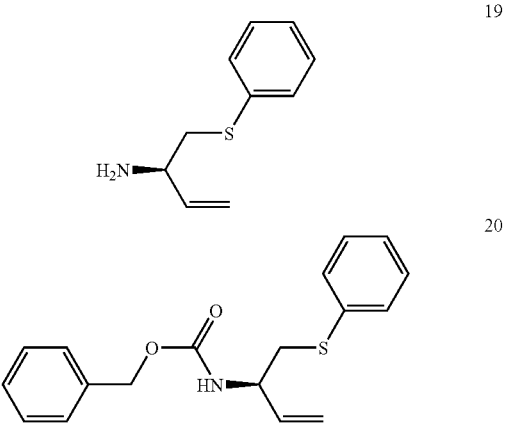

19

20 by substituting a new amine protecting group, i.e., a carbamate group, through conventional procedures.

A compound of formula 14 may then be further converted to a compound of formula 15:

by a two-step process wherein the phthalimide is removed using conventional procedures (i.e., by treatment with ethanolamine) to give 3-amino-4-thiophenyl-1-butene, followed by treatment with carbobenzyloxy chloride (Cbz-Cl) under conventional conditions (e.g., in the presence of base) to give compound 20.

Compound 20 may be converted to a compound of formula 13 or formula 14:

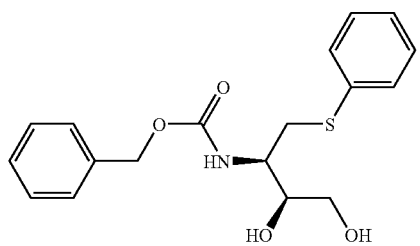

13

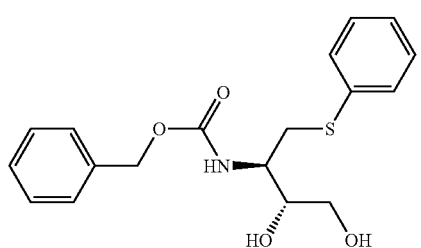

14 or a mixture thereof by stereoselective dihydroxylation of Cbz-3(R)-amino-4-thiophenyl-1-butene 20 using the osmium-containing oxidizing reagent combination of $K_2OsO_2(OH)_4/K_3Fe(CN)_6$, $K_2CO_3$, $NaHCO_3$ and $CH_3SO_2NH_2$ in the presence of a chiral auxiliary reagent. Further, the invention includes a method for converting a compound of formula 13 to a compound of formula 17,21 or 21a

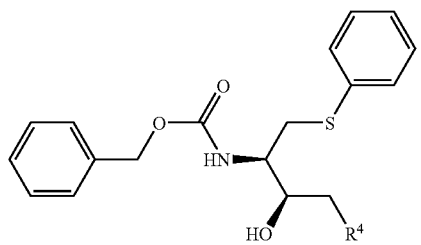

21

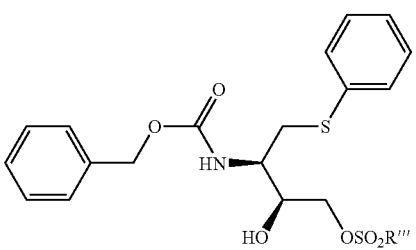

21a wherein $R^4$ is a leaving group in formula 21 and $R'''$ is alkyl or aryl in formula 21a. See Scheme B herein. Further, the invention includes a method of converting a compound of formula 21a to a compound of formula 22 (shown below) and a method of converting a compound of formula 22 to nelfinavir free base, formula 17, according to Scheme B herein.

22

With regard to the respective formulae described above, preferably $R^1$ is alkylcarbonyl, alkoxycarbonyl, arylalkylcarbonyl, arylalkoxycarbonyl, arylcarbonyl, aryloxycarbonyl or arylalkyl and $R^2$ is H. More preferably, $R^1$ is arylalkoxycarbonyl or arylalkyl and $R^2$ is H. Even more preferably, $R^1$ is benzyloxycarbonyl or benzyl and $R^2$ is H. Further, $R^1$ and $R^2$ together with the nitrogen to which they are bound may form a phthalimido or succinimido moiety.

Definitions

As used herein, the terms "comprising" and "including" are used herein in their open, non-limiting sense.

The term "alkyl" refers to a straight- or branched-chain alkyl group having from 1 to 12 carbon atoms in the chain. Exemplary alkyl groups include methyl (Me, which also may be structurally depicted by "/"), ethyl (Et), n-propyl, isopropyl, butyl, isobutyl, sec-butyl, tert-butyl (tBu), pentyl, isopentyl, tert-pentyl, hexyl, isohexyl, and the like.

The term "heteroalkyl" refers to a straight- or branched-chain alkyl group having from 2 to 12 atoms in the chain, one or more of which is a heteroatom selected from S, O, and N. Exemplary heteroalkyls include alkyl ethers, secondary and tertiary alkyl amines, alkyl sulfides, and the like.

The term "alkenyl" refers to a straight- or branched-chain alkenyl group having from 2 to 12 carbon atoms in the chain. Illustrative alkenyl groups include prop-2-enyl, but-2-enyl, but-3-enyl, 2-methylprop-2-enyl, hex-2-enyl, and the like.

The term "alkynyl" refers to a straight- or branched-chain alkynyl group having from 2 to 12 carbon atoms in the chain. Illustrative alkynyl groups include prop-2-ynyl, but-2-ynyl, but-3-ynyl, 2-methylbut-2-ynyl, hex-2-ynyl, and the like.

The term "haloalkyl" refers to a straight- or branched-chain alkenyl group having from 2–12 carbon atoms in the chain and where one or more hydrogens is substituted with a halogen. Illustrative haloalkyl groups include trifluoromethyl, 2-bromopropyl, 3-chlorohexyl, 1-iodo-isobutyl, and the like.

The term "aryl" (Ar) refers to a monocyclic, or fused or spiro polycyclic, aromatic carbocycle (ring structure having ring atoms that are all carbon) having from 3 to 12 ring atoms per ring. Illustrative examples of aryl groups include the following moieties:

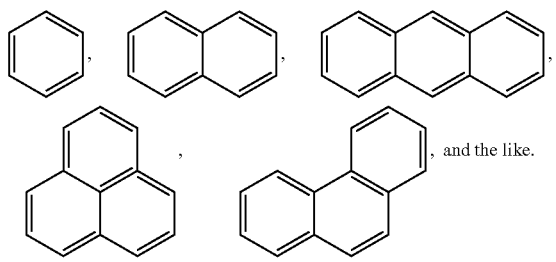

The term "heteroaryl" (heteroAr) refers to a monocyclic, or fused or spiro polycyclic, aromatic heterocycle (ring structure having ring atoms selected from carbon atoms as well as nitrogen, oxygen, and sulfur heteroatoms) having from 3 to 12 ring atoms per ring. Illustrative examples of aryl groups include the following moieties:

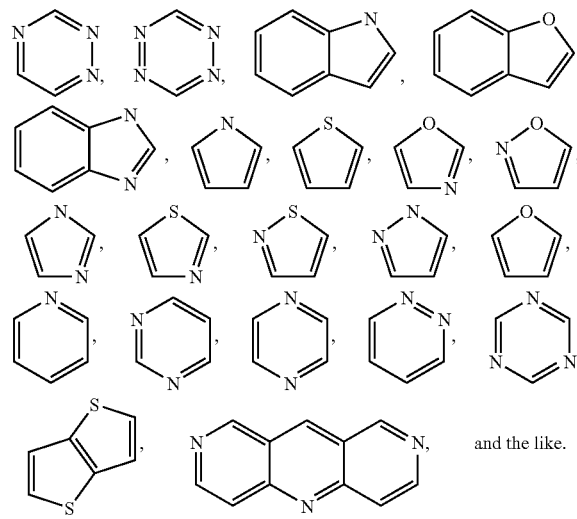

The term "cycloalkyl" refers to a saturated or partially saturated, monocyclic or fused or spiro polycyclic, carbocycle having from 3 to 12 ring atoms per ring. Illustrative examples of cycloalkyl groups include the following moieties:

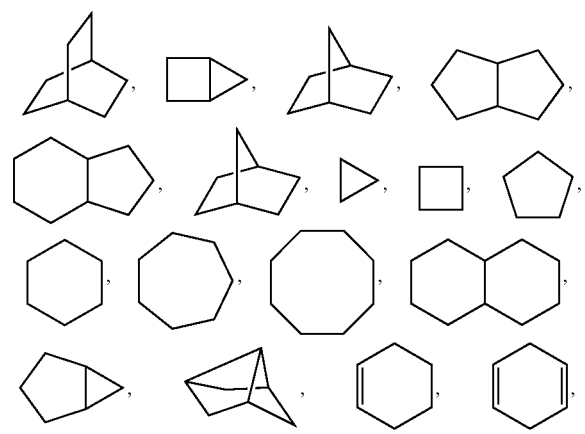

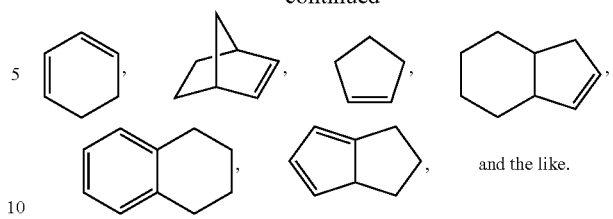

A "heterocycloalkyl" refers to a monocyclic, or fused or spiro polycyclic, ring structure that is saturated or partially saturated and has from 3 to 12 ring atoms per ring selected from C atoms and N, O, and S heteroatoms. Illustrative examples of heterocycloalkyl groups include:

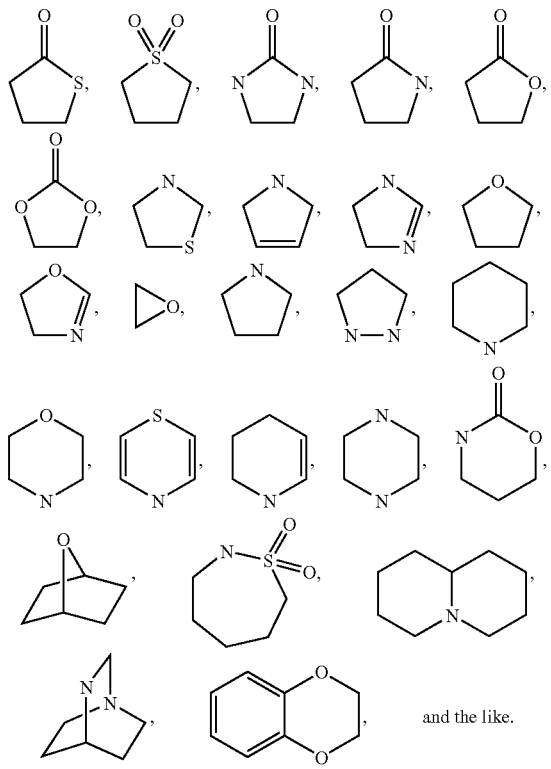

The term "halogen" represents chlorine, fluorine, bromine or iodine. The term "halo" represents chloro, fluoro, bromo or iodo.

The term "substituted" means that the specified group or moiety bears one or more substituents. The term "unsubstituted" means that the specified group bears no substituents. The term "optionally substituted" means that the specified group is unsubstituted or substituted by one or more substituents.

"Alkylthio" is intended to mean the radical —$SR^a$, wherein $R^a$ is an alkyl group, as defined above.

"Arylthio" is intended to mean the radical —$SR^c$, wherein $R^c$ is an aryl group, as defined above.

"Acyl" is intended to mean a —C(O)—R radical, wherein R is an alkyl, cycloalkyl, aryl, heterocycloalkyl or heteroaryl group. "Acyloxy" is intended to mean an —OC(O)—R radical, wherein R is an alkyl, cycloalkyl, aryl, heterocycloalkyl or heteroaryl group. "Thioacyl" is intended to mean a —C(S)—R radical, wherein R is an alkyl, cycloalkyl, aryl, heterocycloalkyl or heteroaryl group. "Sulfonyl" is intended to mean an —SO$_2$— biradical. "Sulfenyl" is intended to mean an —SO-biradical. "Sulfo" is intended to mean an —SO$_2$H radical.

"Hydroxy" is intended to mean the radical —OH. "Amine" or "Amino" is intended to mean the radical —NH$_2$. "Alkylamino" is intended to mean the radical —NHR$_a$, wherein R$_a$ is an alkyl group. "Dialkylamino" is intended to mean the radical —NR$_a$R$_b$, wherein R$_a$ and R$_b$ are each independently an alkyl group, and is intended to include heterocycloalkyl groups, wherein R$_a$ and R$_b$, taken together, form a heterocyclic ring that includes the amine nitrogen. "Alkylenedioxy" is intended to mean the divalent radical —OR$_a$O— which is bonded to adjacent atoms (e.g., adjacent atoms on a phenyl or naphthyl ring), wherein R$_a$ is a lower alkyl group. "Alkoxycarbonyl" is intended to mean the radical —C(O)OR$_a$, wherein R$_a$ is an alkyl group. "Alkylsulfonyl" is intended to mean the radical —SO$_2$R$_a$, wherein R$_a$ is an alkyl group.

"Alkylaminocarbonyl" is intended to mean the radical —C(O)NHR$_a$, wherein R$_a$ is an alkyl group. "Dialkylaminocarbonyl" is intended to mean the radical —C(O)NR$_a$R$_b$, wherein R$_a$ and R$_b$ are each independently an alkyl group.

"Mercapto" is intended to mean the radical —SH.

"Carboxyl" is intended to mean the radical —C(O)OH.

"Keto" or "oxo" is intended to mean the radical =O. "Thioketo" is intended to mean the radical =S.

"Carbamoyl" is intended to mean the radical —C(O)NH$_2$.

"Cycloalkylalkyl" is intended to mean the radical alkyl-cycloalkyl, wherein alkyl and cycloalkyl are defined as above, and is represented by the bonding arrangement present in the groups —CH$_2$-cyclohexane or —CH$_2$-cyclohexene. "Arylalkyl" is intended to mean the radical alkylaryl, wherein alkyl and aryl are defined as above, and is represented by the bonding arrangement present in a benzyl group. "Aminocarbonylalkyl" is intended to mean the radical alkylC(O) NH$_2$ and is represented by the bonding arrangement present in the group —CH$_2$CH$_2$C(O)NH$_2$. "Alkylaminocarbonylalkyl" is intended to mean the radical alkylC(O)NHR$_a$, wherein R$_a$ is an alkyl group and is represented by the bonding arrangement present in the group —CH$_2$CH$_2$C(O)NHCH$_3$. "Alkylcarbonylaminoalkyl" is intended to mean the radical alkylNHC(O)-alkyl and is represented by the bonding arrangement present in the group —CH$_2$NHC(O)CH$_3$. "Dialkylaminocarbonylalkyl" is intended to mean the radical alkylC(O)NR$_a$R$_b$, wherein R$_a$ and R$_b$ are each independently an alkyl group. "Aryloxy" is intended to mean the radical —OR$_c$, wherein R$_c$ is an aryl group. "Heteroaryloxy" is intended to mean the radical —OR$_d$, wherein R$_d$ is a heteroaryl group. "Heteroarylthio" is intended to mean the radical —SR$_d$, wherein R$_d$ is a heteroaryl group.

A "suitable nitrogen-protecting group" is a group that is stable to the reaction conditions used in this invention and that can be removed under conditions that do not induce racemization at the 3-amino or 2-hydroxyl centers of the dihydroxylated compounds prepared herein.

The term "a leaving group" as used herein refers to any group that departs from a molecule in a substitution reaction by breakage of a bond. Examples of leaving groups include, but are not limited to, halides, aryl sulfonates, alkylsulfonates, and triflates.

The alkyl, cycloalkyl, aryl, heterocycloalkyl and heteroaryl groups and the substituents containing these groups, as defined hereinabove, may optionally substituted by at least one substituent. The term "optionally substituted" is intended to expressly indicate that the specified group is unsubstituted or substituted by one or more suitable substituents. Various groups may be unsubstituted or substituted (i.e., they are optionally substituted) as indicated. The term "substituent" or "suitable substituent" is intended to mean any suitable substituent that may be recognized or selected, such as through routine testing, by those skilled in the art.

The compounds of the present invention may have asymmetric carbon atoms. The carbon-carbon bonds in the compounds of the present invention may be depicted herein using a solid line (——), a solid wedge (——), or a dotted wedge (······). The use of a solid line to depict bonds to asymmetric carbon atoms is meant to indicate that all possible stereoisomers at that carbon atom are included. The use of either a solid or dotted wedge to depict bonds to asymmetric carbon atoms is meant to indicate that only the stereoisomer shown is meant to be included. It is possible that compounds of the invention may contain more than one asymmetric carbon atom. In those compounds, the use of a solid line to depict bonds to asymmetric carbon atoms is meant to indicate that all possible stereoisomers are meant to be included. The use of a solid line to depict bonds to one or more asymmetric carbon atoms in a compound of the invention and the use of a solid or dotted wedge to depict bonds to other asymmetric carbon atoms in the same compound is meant to indicate that a mixture of diastereomers is present.

Other features and advantages of the invention will be apparent from the description that follows, which illustrate the invention and its preferred embodiments.

DETAILED DESCRIPTION OF THE INVENTION AND PREFERRED EMBODIMENTS

The method of this invention comprises treatment of an amino-butene with an osmium-containing oxidizing agent to provide the corresponding dihydroxyamino-butane, according to the following general scheme (Scheme A)

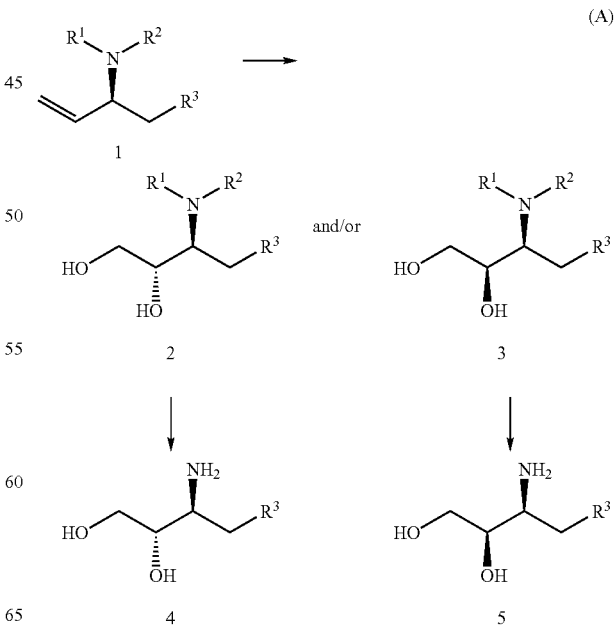

wherein:
R$^1$ is a suitable nitrogen protecting group; and
R$^2$ is H or
R$^1$ together with R$^2$ form a suitable nitrogen protecting group; and
R$^3$ is thioalkyl or thioaryl.

When used in the preparation of nelfinavir, R$^3$ is preferably an thioaryl group or a moiety that can be converted into an thioaryl group. More preferably, R$^3$ is a thiophenyl group (—S-Ph), as the thiophenyl group is present in the nelfinavir free base compound.

In the processes described herein involving the imidoyl protection, e.g., phthalmide, succinimide or N-diformyl protection on the nitrogen, a high degree of stereoselection is obtained in the dihydroxylation step. If the phthalmamid protection group is removed and substituted with other protection groups, e.g., carbamate, alkyl or amide, the high degree of stereoselection is not achieved. Thus, it is preferred to have imide-type protection on the nitrogen prior to dihydroxylation.

This invention also provides compounds that are useful in the method described herein having the formula 1, 2, 3, 4 and 5, described above.

Intermediate Compounds

Intermediate compounds in accordance with the invention include tautomeric and stereoisomeric forms of the compounds of Formula 1, which may be readily obtained using techniques known in the art. For example, optically active (R) and (S) isomers may be prepared via a stereospecific synthesis, e.g., using chiral synthons and chiral reagents, or racemic mixtures may be resolved using conventional techniques.

It is understood that while a compound may exhibit the phenomenon of tautomerism, the formula drawings within this specification expressly depict only one of the possible tautomeric forms. It is therefore to be understood that a formula is intended to represent any tautomeric form of the depicted compound and is not to be limited merely to a specific compound form depicted by the structural formula.

It is also understood that a compound of Formula 1 may exist as an "E" or "Z" configurational isomer, or a mixture of E and Z isomers. It is therefore to be understood that a formula is intended to represent any configurational form of the depicted compound and is not to be limited merely to a specific compound form depicted by the formula drawings.

Some of the inventive compounds may exist as single stereoisomers (i.e., essentially free of other stereoisomers), racemates, and/or mixtures of enantiomers and/or diastereomers. All such single stereoisomers, racemates and mixtures thereof are intended to be within the scope of the present invention. In one preferred embodiment, the inventive compounds that are optically active (i.e., enantiomerically or diastereomerically enriched, as described herein) are used in optically pure form.

Additionally, Formula 1 is intended to cover, where applicable, solvated as well as unsolvated forms of the compounds. Thus, each formula includes compounds having the indicated structure, including the hydrated as well as the non-hydrated forms.

Exemplary substituted aryls contain with one or more substituents, preferably one to three substituents, independently selected from halo, hydroxy, mercapto, thioether, nitro (NO$_2$), amino, aryloxyl, halogen, hydroxyl, alkoxyl, halo (C$_1$–C$_4$)alkyl, C$_1$–C$_4$ alkyl, C$_1$–C$_4$ alkoxy, carboxyl, C$_1$–C$_4$ alkoxycarbonyl, carbamoyl, N—(C$_1$–C$_4$)alkylcarbamoyl, amino, C$_1$–C$_4$alkylamino, di(C$_1$–C$_4$)alkylamino or a group of the formula —(CH$_2$)$_a$—R$^7$ where a is 1, 2, 3 or 4; and R$^7$ is hydroxy, C$_1$–C$_4$ alkoxy, carboxyl, C$_1$–C$_4$ alkoxycarbonyl, amino, carbamoyl, C$_1$–C$_4$ alkylamino, di(C$_1$–C$_4$)alkylamino, aryl, saturated or partially saturated heterocycles, acyl, morpholino(C$_1$–C$_4$)alkoxy carbonyl and pyridyl (C$_1$–C$_4$)alkoxycarbonyl.

Exemplary substituted alkyls contain one or more substituents selected from aryl, cycloalkyl, heterocycloalkyl, heteroaryl, nitro, amino, cyano, halo, hydroxyl, alkoxy, aryloxy, heterocycloalkoxy, heteroaryloxy, alkylcarbonyl, alkyloxycarbonyl, alkylcarbonyloxy, arylcarbonyl, arylcarbonyloxy, aryloxycarbonyl, heteroarylcarbonyl, heteroarylcarbonyloxy, heteroaryloxycarbonyl, heterocycloalkylcarbonyl, heterocycloalkylcarbonyloxy, heterocycloalkyoxycarbonyl, alkylamino, arylamino, heterocycloalkylamino, heteroarylamino, dialkylamino, alkylaminocarbonyl, arylaminocarbonyl, heterocycloalkylaminocarbonyl, heteroarylaminocarbonyl, dialkylaminocarbonyl, mercapto, alkylthio, arylthio and heteroarylthio. Exemplary substituted alkyl groups include lower alkylmercaptoalkyl, alkylthioalkyl, arylthioalkyl, nitroalkyl, aminoalkyl, aryloxylalkyl, acyl, halo(C$_1$–C$_4$)alkyl, hydroxy (C$_1$–C$_4$)alkyl, C$_1$–C$_4$ alkylthio(C$_1$–C$_4$)alkyl, heteroaryl(C$_1$–C$_4$)alkyl, heterocycloalkyl(C$_1$–C$_4$)alkyl and aryl(C$_1$–C$_4$)alkyl groups, such as chloromethyl, 2-bromoethyl, 1-chloroisopropyl, 3-fluoropropyl, 2,3-dibromobutyl, 3-chloroisobutyl, iodo-t-butyl, trifluoromethyl, hydroxymethyl, 2-hydroxyethyl, 3-hydroxypropyl, 2-hydroxyisopropyl, 4-hydroxybutyl, methylthiomethyl, ethylthiomethyl, propylthiopropyl, sec-butylthiomethyl, pyrrolylmethyl, quinolinylmethyl, 1-indolylethyl, 2-furylethyl, 3-thien-2-ylpropyl, 1-imidazolylisopropyl, 4-thiazolylbutyl, phenylmethyl, 2-phenylethyl, 3-naphthyl-propyl, 1-naphthylisopropyl, 4-phenylbutyl and the like.

If an inventive compound is a base, a desired salt may be prepared by any suitable method known in the art, including treatment of the free base with an inorganic acid, such as hydrochloric acid, hydrobromic acid, sulfuric acid, nitric acid, phosphoric acid, and the like, or with an organic acid, such as acetic acid, maleic acid, succinic acid, mandelic acid, fumaric acid, malonic acid, pyruvic acid, oxalic acid, glycolic acid, salicylic acid, pyranosidyl acid, such as glucuronic acid or galacturonic acid, alpha-hydroxy acid, such as citric acid or tartaric acid, amino acid, such as aspartic acid or glutamic acid, aromatic acid, such as benzoic acid or cinnamic acid, sulfonic acid, such as p-toluenesulfonic acid or ethanesulfonic acid, or the like.

If an inventive compound is an acid, a desired salt may be prepared by any suitable method known to the art, including treatment of the free acid with an inorganic or organic base, such as an amine (primary, secondary, or tertiary); an alkali metal or alkaline earth metal hydroxide; or the like. Illustrative examples of suitable salts include organic salts derived from amino acids such as glycine and arginine; ammonia; primary, secondary, and tertiary amines; and cyclic amines, such as piperidine, morpholine, and piperazine; as well as inorganic salts derived from sodium, calcium, potassium, magnesium, manganese, iron, copper, zinc, aluminum, and lithium.

All compounds of this invention contain at least one chiral center and may exist as single stereoisomers, and/or mixtures of enantiomers and/or diastereomers. All such stereoisomers, diastereomers and mixtures thereof are intended to be encompassed within the scope of the present invention. Where the stereochemistry of the chiral carbons present in the chemical structures illustrated herein is not specified, the chemical structure is intended to encompass compounds containing either stereoisomer of each chiral carbon.

When used describe a particular compound, the term "optically active" is used herein to indicate that the compound is enantiomerically or diastereomerically enriched. Compounds that are enantiomerically enriched contain greater than 50% of a single stereoisomer, and preferably contain greater than 75% of a single stereoisomer. Compounds that are diastereomerically enriched contain greater than 50% of a single stereoisomer of each chiral carbon center present in the diastereomer, and preferably contain greater than 75% of a single stereoisomer of each chiral carbon present in the diastereomer. Preferably, however, the compounds are present in optically pure form.

When used describe a particular compound, the term "optically pure" is used herein to indicate that the compound is substantially enantiomerically or diastereomerically pure. Compounds that are substantially enatomerically pure contain at least 90% of a single isomer and preferably contain at least 95% of a single isomer. Compounds that are substantially diastereomerically pure contain at least 90% of a single isomer of each chiral carbon center present in the diastereomer, and preferably contain at least 95% of a single isomer of each chiral carbon. More preferably, the optically pure compounds in this invention contain at least 97.5% of a single isomer and most preferably contain at least 99% of a single isomer. Compounds identified herein as single stereoisomers are meant to describe compounds that are present in a form that contains at least 90% of a single isomer.

The dihydroxylation reaction in the method of this invention may be conducted using stoichiometric or catalytic amounts of the osmium-containing oxidizing agent. If catalytic amounts of the oxidizing agent are used, the dihydroxylation may be conducted in the presence of stoichiometric amounts of a second oxidizing agent that serves as an osmium re-oxidizing agent. If a stoichiometric amount of the oxidizing agent is used, the oxidizing reagent is used in an amount that is equi-molar to the amount of butene present in the reaction mixture. If a catalytic amount of the oxidizing agent is used, the oxidizing reagent is used in an amount that is about 1% to about 15% of the molar amount of butene present in the reaction mixture.

Preferably the dihydroxylation is conducted using catalytic amounts of the osmium-containing oxidizing agent in combination with potassium ferricyanide. A particularly useful osmium oxidizing agent combination is $K_2OsO_2(OH)_4$/$K_3Fe(CN)_6$, $K_2CO_3$, $NaHCO_3$ and $CH_3SO_2NH_2$, which may be used in the presence of $DHQD_2PHAL$ as a chiral auxiliary reagent.

Preferably, the amino-moiety of the amino-butene is protected with a protecting group prior to treatment with the oxidizing agent. In formula 1, above, $R^1$ and/or $R^2$ represent a suitable nitrogen protecting group. Thus, for example referring to scheme A herein, compounds 2 and 3 are the dihydroxylated forms of compound 1. Suitable nitrogen protection groups $R^1$ and/or $R^2$ are those that when removed to form compounds 4 and/or 5 do not induce racemization. The nitrogen-protecting group may be removed at a suitable point in the reaction sequence of the method to provide a desired intermediate or target compound. Suitable nitrogen-protecting groups and the methods for protecting and de-protecting an amino moiety are known to those skilled in the art; examples of which may be found in T. Greene and P. Wuts, Protecting Groups in Chemical Synthesis (3rd Ed.), John Wiley & Sons, NY (1999), which is incorporated herein by reference in its entirety. In some instances, a nitrogen-protecting group may be specifically selected to be reactive under the reaction conditions used in the methods of this invention. Under these circumstances, the reaction conditions convert the selected protecting group into a substituent that is either useful as an intermediate compound in this invention or is a desired amino-substituent in a target compound.

Generally, the nitrogen protecting groups may be selected from the moieties wherein $R^1$ is alkylcarbonyl, alkoxycarbonyl, arylalkylcarbonyl, arylalkoxycarbonyl arylcarbonyl, aryloxycarbonyl or arylalkyl and $R^2$ is H. Exemplary suitable nitrogen protecting groups include those moieties wherein $R^1$ is benzyloxycarbonyl, benzylcarbonyl, t-butylcarbonyl, t-butyloxycarbonyl, allyl, benzyl or substituted benzyl groups (e.g., 4-methoxybenzyl) and $R^2$ is H. In especially preferred embodiments, $R^1$ is selected from arylalkoxycarbonyl (e.g., benzyloxycarbonyl) or arylalkyl (e.g., benzyl) and $R^2$ is H. In other preferred embodiments, $R^1$ and $R^2$ together with the nitrogen to which they are bound form a phthalimido

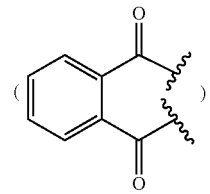

or succinimido

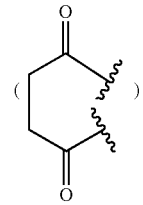

moiety.

As indicated above, the dihydroxylation reaction in the method of this invention preferably occurs stereoselectively, wherein one of the possible diastereomeric products is formed in preference to the other. Thus, the dihydroxybutane product obtained in the method of this invention is a mixture of both R and S isomers, wherein the two isomers are present in unequal concentrations. The amino-butene used herein is substantially enantiomerically pure (containing at least 95% of a single enantiomer). Accordingly, the resulting aminobutane diol product is obtained as a mixture of diastereomers, wherein the diastereomeric excess is consistent with the enantiomeric purity of the product. Preferably, the diastereomeric ratio should reflect the enantiomeric integrity of the product. Optionally, the diastereomers may be separated using conventional procedures to obtain a diastereomerically pure product. Exemplary methods that may be useful for the separation of diastereomers prepared by the method of this invention include chromatography and crystallization/re-crystallization. Other useful methods may be found in "Enantiomers, Racemates, and Resolutions," J. Jacques et al., 1981, John Wiley and Sons, New York, N.Y., the disclosure of which is incorporated herein by reference. The stereoselectivity of the dihydroxylation reaction is achieved by conducting the reaction in the presence of a chiral auxiliary reagent. As used herein the term "chiral auxiliary reagent" refers to an optically active compound that is stable to the dihydroxylation reaction conditions used herein and is capable of influencing the stereochemical outcome of the dihydroxylabon reaction. Advantageously, the dihydroxylation reaction may be conducted using a quinine or quinidine alkaloid as chiral auxiliary reagent to form, stereoselectively, 1,2(R)-dihydroxy-3(R)amino-butanes or 1,2(S)-dihydroxy-3(R)amino-butanes. Examples of chiral auxiliary reagents that may be useful in the dihydroxylation reaction of this invention include dihydroquinidine 1,4-phthalazinediyl diether ((DHQD)$_2$PHAL), hydroquinone 2,5-diphenyl-4,6-pyrimidinediyl diether, (DHQ)$_2$PYR, hydroquinone anthraquinone-1,4-diyl diether (DHQ)$_2$AQN and the optically active reagents disclosed in WO 93/07142, the disclosure of which is incorporated herein by reference. Particularly useful chiral auxiliary reagents include: (DHQD)$_2$PHAL, (DHQ)$_2$PYR, and (DHQ)$_2$AQN. Generally, the dihydroxylation reaction is conducted using the chiral auxiliary reagent in an amount that is about 1% to about 6% of the molar amount of butene present in the reaction mixture.

Generally, the dihydroxylation reaction may be conducted in polar solvents or mixtures of polar solvents and organic solvents or mixtures of organic solvents and water. Preferably, the reaction may be conducted in polar protic solvents. Useful solvents include t-butanol, acetone, t-butanol/water and acetone/water. The dihydroxyation reaction may be conducted at any suitable temperature. Generally, the reaction may be conducted at temperatures from about 0° C. to about room temperature.

In one embodiment of this invention, a protected (R)-amino-butene is stereoselectively converted into an aminohydroxy butanol using DHQD$_2$PHAL as the chiral auxiliary reagent. A useful starting material for this process is the commercially available (from NSC Technologies, Mt. Prospect, Ill.) phthalimide of 3(R)-amino-4-hydroxy-1-butene. This material contains a 4-hydroxyl group that is a useful precursor in the preparation of nelfinavir, wherein the 4-hydroxyl moiety may be converted into a thiophenyl substituent that will be useful for the preparation of nelfinavir. This conversion process may be accomplished by first transforming the hydroxyl group into a leaving group, then replacing the leaving group with a thiophenyl group. Substitution processes of this type are well studied and may be accomplished using any of a variety of transformations. Leaving groups refer to any group that departs from a molecule in a substitution reaction by breakage of a bond, and include, but are not limited to, halides, aryl sulfonates, alkylsulfonates, and triflates. For example, the hydroxyl group may be converted into a halo moiety, a mesylate (—OSO$_2$CH$_3$), a triflate (—OSO$_2$CF$_3$), a tosylate (—OSO$_2$-(p-tolyl)) or other commonly recognized leaving groups that may be replaced by a nucleophilic reagent. The nucleophilic reagent may be in any form, for example, a reagent containing a nucleophilic moiety, particularly, a thiophenoxide moiety (e.g., PH—S$^-$K$^+$), or an organometallic reagent.

This embodiment of the method of this invention is exemplified by the conversion of the 3(R)-phthalimido-4-hydroxy-1-butene 6 to the 3(R)-phthalimido-4-thiophenyl-butene 8 as illustrated below:

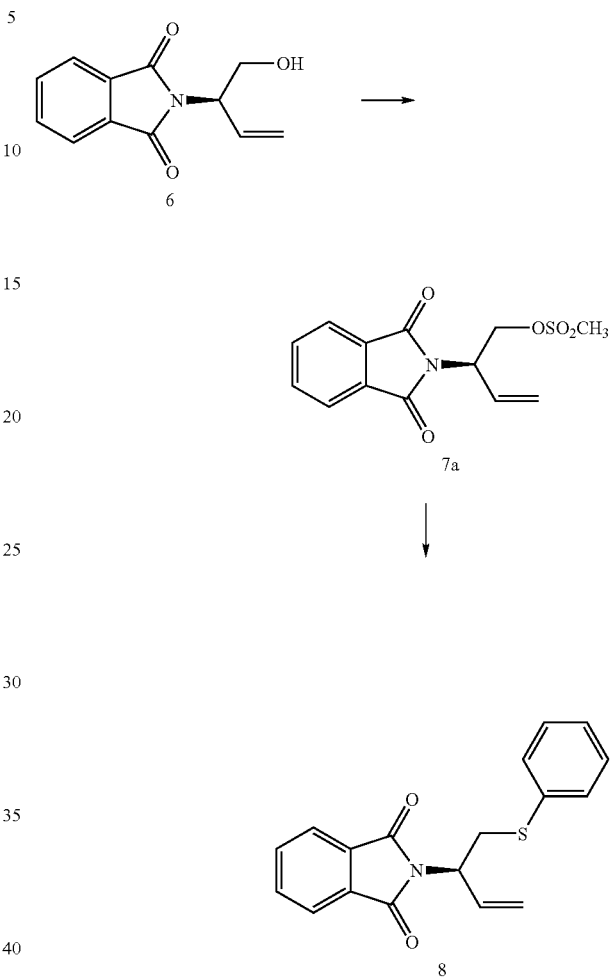

In this method, the hydroxy-butene 6 is first converted to a butene-mesylate 7a by treatment with methane sulfonyl chloride, under conventional conditions (e.g., in the presence of an amine base, e.g., triethyl amine or diisopropyl ethylamine, in a polar aprotic solvent, e.g., N,N-dimethyl formamide, N,N-dimethylacetamide, methyl-t-butyl ether, or tetrahydrofuran). One skilled in the art will recognize that the chemical transformations in the methods of this invention may be performed using any pharmaceutically acceptable solvent that is compatible with the intermediate substrates and the transformation conducted. The resulting mesylate may then be treated with thiophenoxide (formed in situ using thiophenol and a non-nucleophilic base, e.g. diisopropyl ethylamine, potassium carbonate, and the like) in a polar aprotic solvent, to form the thiophenyl-butene compound 8. Stereoselective dihydroxylation of compound 8 can be conducted using the osmium-containing oxidizing reagent combination of K$_2$OsO$_2$(OH)$_4$/K$_3$Fe(CN)$_6$, K$_2$CO$_3$, NaHCO$_3$ and CH$_3$SO$_2$NH$_2$ in the presence of DHQD$_2$PHAL as the chiral auxiliary reagent, to provide the 1,2(R)-dihydroxy-3(R)phthalimido-4-(phenylthio)-butane 9 and 1,2(S)-dihydroxy-3(R)-phthalimido-4-(phenylthio)-butane 10 in a 13:1 ratio.

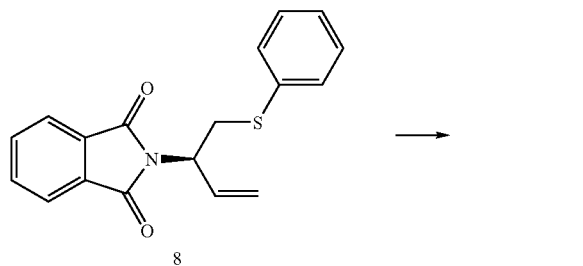

8

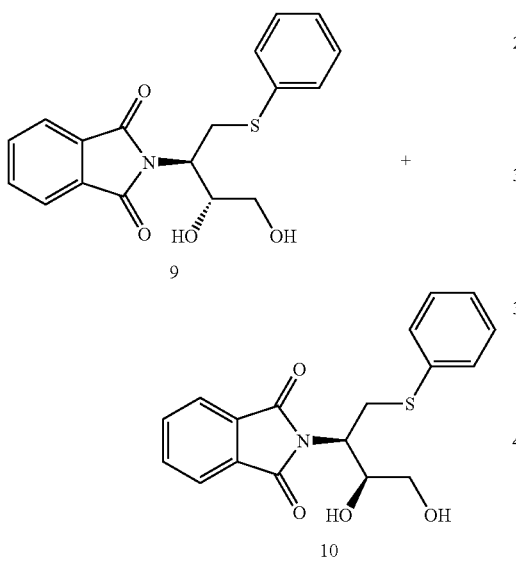

9

+

10

Removal of the phthalimide amino-protecting group may be conducted using any conventional method that does not induce racemization at the 3-amino or 2-hydroxyl centers of the butane compound. General methods for removing protecting groups are described in Greene and Wuts, supra. For example, treatment with methylamine converts phthalimide 9 to dihydroxy-amino-butane 11.

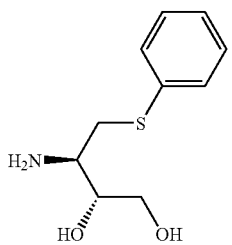

11

This compound may be subsequently derivatized and transformed into other intermediate compounds useful for the preparation of nelfinavir or nelfinavir mesylate.

One skilled in the art will recognize that the stereoisomer that is stereoselectively formed by the dihydroxylation method of this invention may be changed by using a different chiral auxiliary reagent. One skilled in the art will also recognize that stereoselective dihydroxylation of 3(R)-amino-butenes containing different nitrogen-protecting groups and/or different butene substituents, in the presence of different auxiliary reagents, may produce mixtures of 1,2(R)-dihydroxy-3(R)-amino-butanes and 1,2(S)-dihydroxy-3(R)-amino-butanes in different ratios. That is, the stereoselectivity of the dihydroxylation reaction may vary depending on the specific substrate and the specific chiral auxiliary reagent used in the reaction (e.g. using different quinine or quinidine alkaloid chiral auxiliary reagents). However, based on the teachings herein and through routine experimentation (e.g., preparing compounds having different nitrogen protecting groups or compounds having different substituents and conducting the dihydroxylation reaction using different chiral auxiliary reagents), one skilled in the art will be able to select a chiral auxiliary reagent that stereoselectively provides the desired stereoisomer of a specific amino-butene.

For example, the dihydroxylation of 3(R)-amino-butenes may be conducted to stereoselectively provide 1,2(S)-dihydroxy-3(R)-amino-4-(phenylthio)-butane, using a chiral auxiliary reagent other than $DHQD_2PHAL$ and optionally, using an amino-butene having a nitrogen-protecting group different from the phthalimide, illustrated above. The nitrogen protecting groups may be exchanged, if desired, by converting the phthalimide-protected 3(R)-amino-4-thiophenyl-1-butene 8, prepared as described above, to a Cbz-protected 3(R)-amino-4-thiophenyl-1-butene prior to dihydroxylation. Specifically, Cbz-protected 3(R)-amino-4-thiophenyl-1-butene 20 may be prepared from the phthalimide-protected 3(R)-amino-4-thiophenyl-1-butene 8, above, by a two-step process wherein the phthalimide is removed using conventional procedures (i.e., by treatment with ethanolamine) to give 3-amino-4-thiophenyl-1-butene, followed by treatment with carbobenzyloxy chloride (Cbz-Cl) under conventional conditions (e.g., in the presence of base). Stereoselective dihydroxylation of Cbz-3(R)-amino-4-thiophenyl-1-butene 20 may be conducted using the osmium-containing oxidizing reagent combination of $K_2OsO_2(OH)_4/K_3Fe(CN)_6$, $K_2CO_3$, $NaHCO_3$ and $CH_3SO_2NH_2$ in the presence of quinuclidine as the chiral auxiliary reagent, to provide the 1,2(S)-dihydroxy-3(R)-Cbz-4-(phenylthio)-butane 13 and 1,2(R)-dihydroxy-3(R)-Cbz-4-(phenylthio)-butane 14, in a 4:1 ratio.

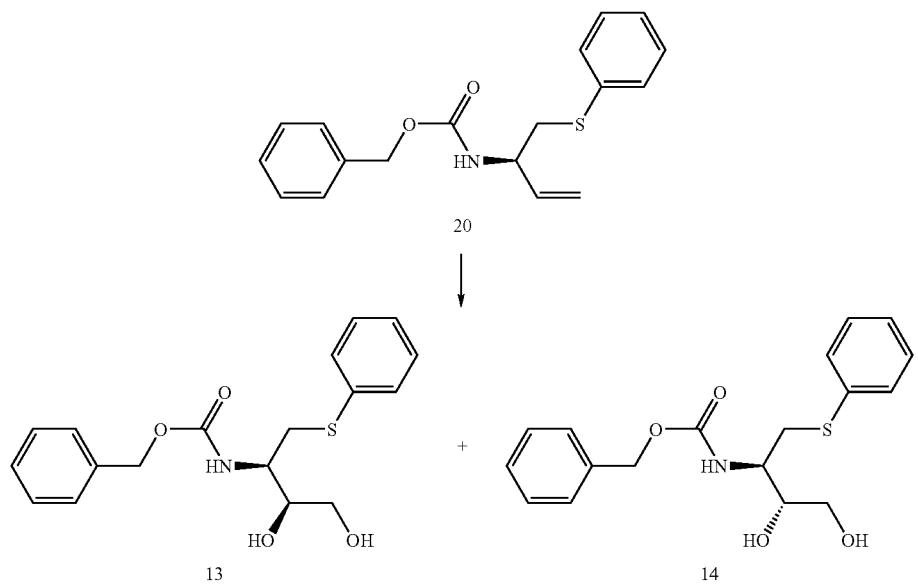

Advantageously, the 2-hydroxyl moiety of the major dihydroxybutane 13 possesses the same absolute configuration as the hydroxyl moiety in nelfinavir. Accordingly, this material is also useful for the preparation of nelfinavir or nelfinavir mesylate.

The rate of dihydroxylation of the amino-butenes described herein may be accelerated by the addition of alkylamines. For example, it has been discovered that use of DABCO (1,4-diazabicyclo[2.2.2]octane) accelerates the rate of dihydroxylation. Moreover, it has been discovered that complex alkyl amines, such as DABCO may be used as chiral auxiliary reagents in the method of this invention. For example, dihydroxylation of the Cbz-amino-butene 20 using $K_2OsO_2(OH)_4/K_3Fe(CN)_6$, $K_2CO_3$, $NaHCO_3$ and $CH_3SO_2NH_2$ in the presence of DABCO, as the chiral auxiliary reagent, provided a 30% yield of the 1,2(S)-dihydroxy-3(R)-Cbz-4-(phenylthio)-butane 13 and 1,2(R)-dihydroxy-3(R)-Cbz-4-(phenylthio)-butane 14 in a ratio of about 2:1. Generally, acceleration of the dihydroxylation reaction may be achieved by using DABCO in an amount that is about 10% about 100% of the molar amount of butene present in the reaction mixture. When used as a chiral auxiliary reagent, DABCO may be used in amounts that are the same as that of the other chiral auxiliary reagents, described above.

Accordingly, a compound of formula 1 is stereoselectively converted to a compound of formula 2:

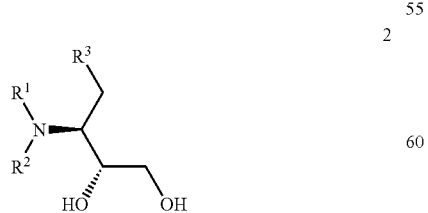

2 by treating the compound of formula 1 with an osmium-containing oxidizing reagent combination of $K_2OsO_2(OH)_4/K_3Fe(CN)_6$, $K_2CO_3$, $NaHCO_3$ and $CH_3SO_2NH_2$ in the presence of $DHQD_2PHAL$ as a chiral auxiliary reagent to provide the compound represented by formula 2.

The compound of formula 1 may also be stereoselectively converted to a compound of formula 3:

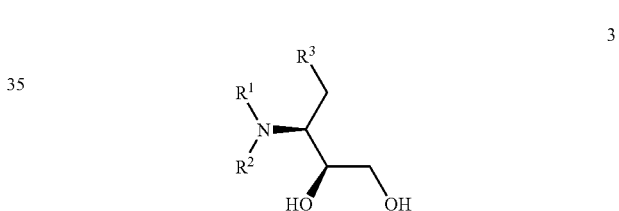

3 by treating a compound of formula 1 with an osmium-containing oxidizing reagent combination of $K_2OsO_2$ $(OH)_4/K_3Fe(CN)_6$, $K_2CO_3$, $NaHCO_3$ and $CH_3SO_2NH_2$ in the presence of $DHQD_2PHAL$ as a chiral auxiliary reagent to provide the compound represented by formula 3.

The compound of formula 2 may also be converted to a compound of formula 4, while the compound of formula 3 may be converted to a compound of formula 5 by removing the nitrogen protection group without inducing racemization to provide the compounds represented by formula 4 or 5, respectively.

The compound of formula 6:

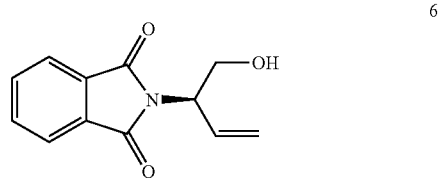

6 is converted to a compound of formula 8, by treating a compound of formula 6 with methane sulfonyl chloride in the presence of an amine base in a polar aprotic solvent to provide butene-mesylate 7a; and

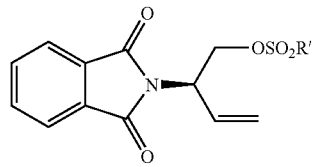

7a treating butene-mesylate 7a with thiophenoxide, wherein the thiophenoxide is formed in situ using thiophenol and a non-nucleophilic base in a polar aprotic solvent, to provide thiophenyl-butene 8

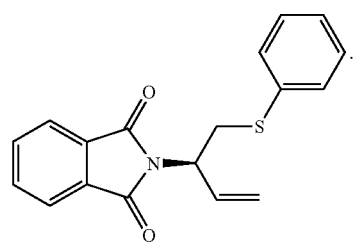

8

In particular, the compound of formula 6:

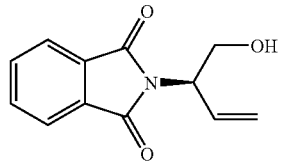

6 is converted to a compound of formula 7a:

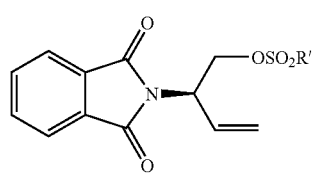

7a wherein R' is alkyl or aryl, preferably, methyl, trifluoromethyl or p-tolyl, and converting the compound of formula 7a, to a compound of formula 8 by treating the compound of formula 6 or 7a with an osmium-containing oxidizing reagent combination of $K_2OsO_2(OH)_4/K_3Fe(CN)_6$, $K_2CO_3$, $NaHCO_3$ and $CH_3SO_2NH_2$ in the presence of $DHQD_2PHAL$ as a chiral auxiliary reagent to provide the compound represented by formula 7a or 8, respectively.

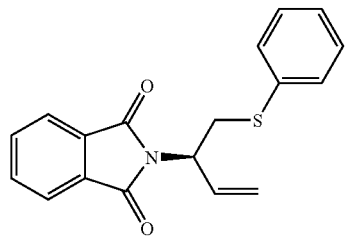

8

In turn, the compound of formula 8 is stereoselectively converted to the compound of formula 9:

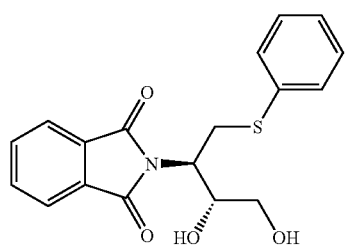

9 or to a compound of formula 10:

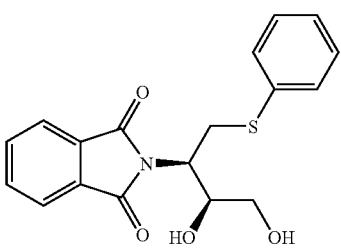

10 or a mixture thereof, by treating a compound of formula 8 with an osmium-containing oxidizing reagent combination of $K_2OsO_2(OH)_4/K_3Fe(CN)_6$, $K_2CO_3$, $NaHCO_3$ and $CH_3SO_2NH_2$ in the presence of $DHQD_2PHAL$ as a chiral auxiliary reagent to provide the compound represented by formula 9 or 10.

Alternatively, the compound of formula 9 is converted to the compound of formula 11:

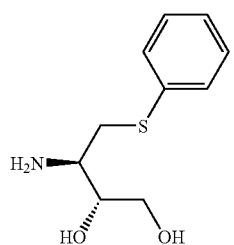

11 and/or the compound of formula 10 is converted to the compound of formula 12:

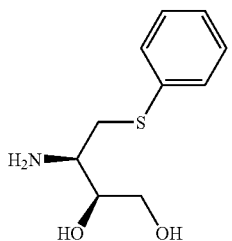

12

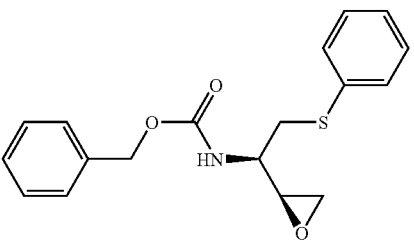

15 by treating the respective starting compounds with a reagent that de-protects the nitrogen protection group to provide the compound represented by formula 11 or 12, respectively, without inducing racemization.

Further, a compound of formula 9 is converted to a compound of formula 14:

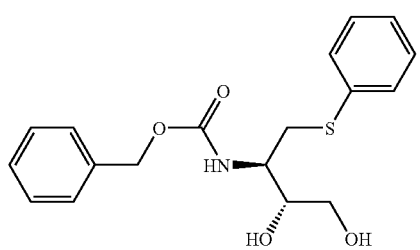

14 and/or a compound of formula 11 is converted to a compound of formula 14 by treating the respective starting materials with reagents that will open the bicyclic ring of the nitrogen protecting group, e.g., the compound 9 to 14 conversion, or add a nitrogen protecting group in a single step, e.g., converting compound 11 to 14. In similar fashion to the formula 9 to 14 conversion, a compound of formula 10 is converted to a compound of formula 13

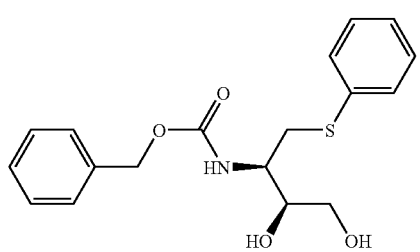

13 by deprotecting the nitrogen followed by benzocarbamate formation. A compound of formula 12 is converted to a compound of formula 13 by treating the respective starting compound by using the carbamate formation step described above.

The invention also includes the method of converting a compound of formula 14 to a compound of formula 15:

by treating the compound of formula 14 with methylphenyl sulfonyl chloride and an amine base solvent followed by treatment with an aqueous base to yield the compound of formula 15. The compound of formula 15 is further converted to a compound of formula 16

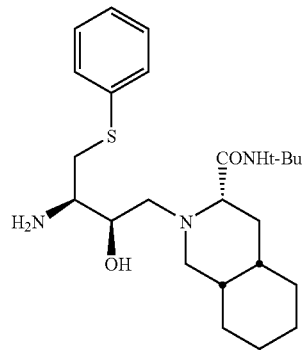

16 by heating a solution comprising (2S, 3R)-3-benzyloxycarbonylamino-4-phenylthio-1-buteneoxide 15 and (3S, 4aS, 8aS)-decahydroisoquinoline-3-carboxylic acid t-butylamide in isopropyl alcohol; adding an aqueous solution of 2N potassium hydroxide; adding toluene and washing with water and 1N hydrochloric acid; extracting and combining the aqueous layers; and drying the extracted product to provide (3S, 4aS, 8aS)-2-((2R, 3R)-3-amino-2-hydroxy-4-phenylthiobutyl)-decahydroisoquinaline-3-carboxylic acid t-butylamide 16.

The compound of formula 16 is then converted to nelfinavir and/or nelfinavir mesylate, compounds having the formula 17 and 18, respectively,

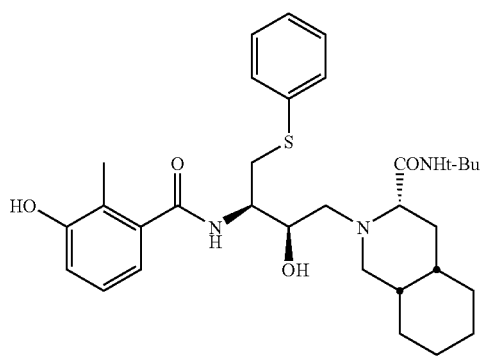

17

-continued

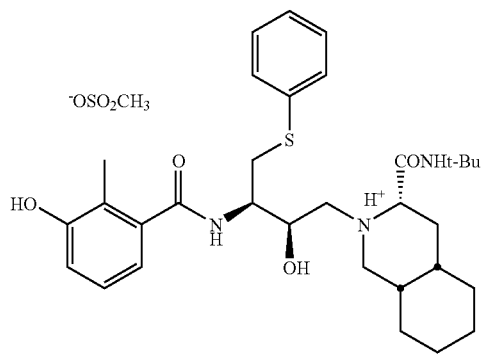

18 according to the methods described in WO 97/11937 and WO 97/11938, which are incorporated herein by reference.

The compound of formula 8 is alternatively converted to a compound of formula 20:

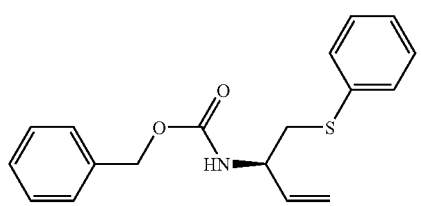

20 by first converting the compound of formula 8 to a compound of formula 19:

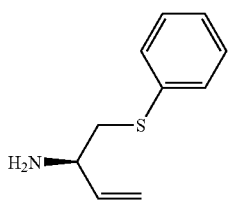

19 and then converting the compound of formula 19 to a compound of formula 20 by adding different protection groups as described herein. The compound of formula 8 is a preferred substrate for adding different protection groups as it provides high stereoselection in the subsequent dihydroxylation step.

The compound of formula 20

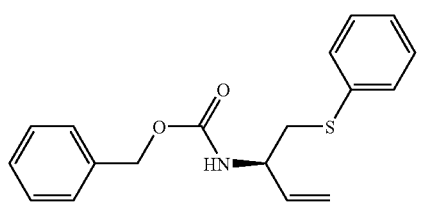

20 is also stereoselectively converted to a compound of formula 13:

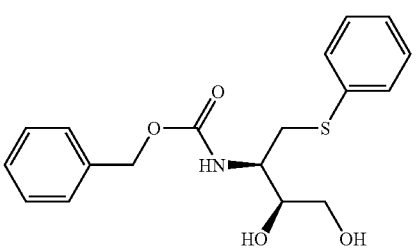

13 or to a compound of formula 14:

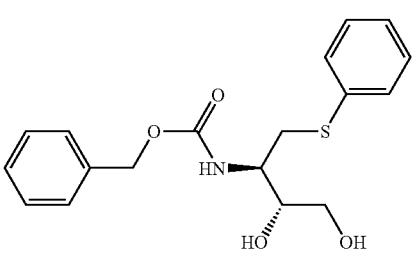

14 or a mixture thereof, by treating the respective starting compounds with an osmium-containing oxidizing reagent combination of $K_2OsO_2(OH)_4$/$K_3Fe(CN)_6$, $K_2CO_3$, $NaHCO_3$ and $CH_3SO_2NH_2$ in the presence of $DHQD_2PHAL$ as a chiral auxiliary reagent to provide the compound represented by formula 13 or 14, respectively.

In similar fashion, a compound of formula 13 is converted to a compound of formula 21:

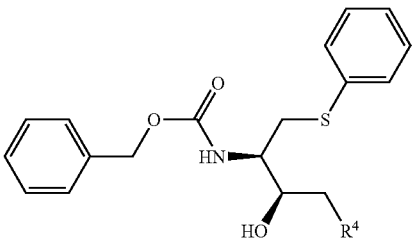

21 wherein $R^4$ is a leaving group as defined herein. In particular, the compound of formula 21a is formed by reacting the compound of formula 13 with p-toluenesulfonyl chloride (tosyl chloride) and a base, such as triethylamine, in methylene chloride. Preferably $R^4$ is chloro, bromo, —$OSO_2$—R', wherein R' is alkyl or aryl, preferably, methyl, trifluoromethyl or p-tolyl.

The compound of formula 20 is converted to a compound of formula 21a:

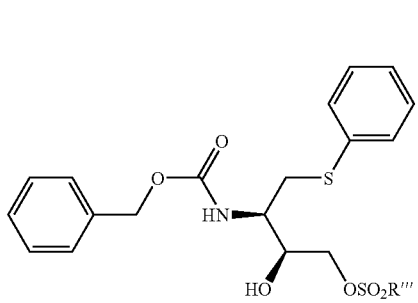

wherein R''' is alkyl or aryl, and preferably, methyl, trifluoromethyl or p-tolyl, and converting the compound of formula 21a to a compound of formula 22:

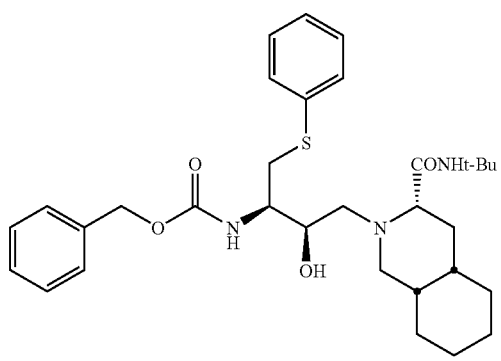

by treating the respective starting compounds with an osmium-containing oxidizing reagent combination of $K_2OsO_2(OH)_4/K_3Fe(CN)_6$, $K_2CO_3$, $NaHCO_3$ and $CH_3SO_2NH_2$ in the presence of $DHQD_2PHAL$ as a chiral auxiliary reagent to provide the compound represented by formula 21a or 22, respectively. The reaction may take place according to the following scheme (Scheme B).

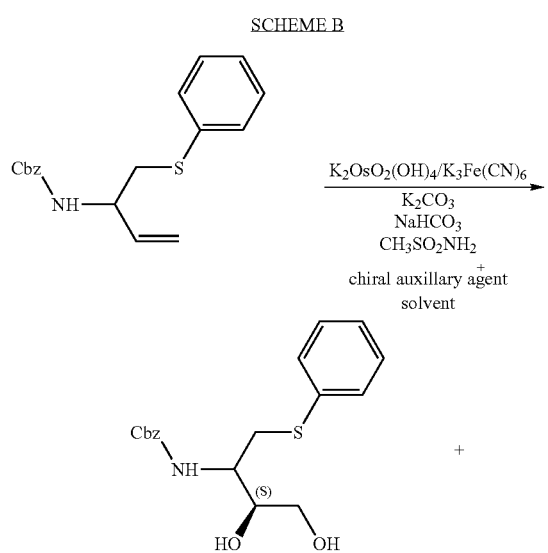

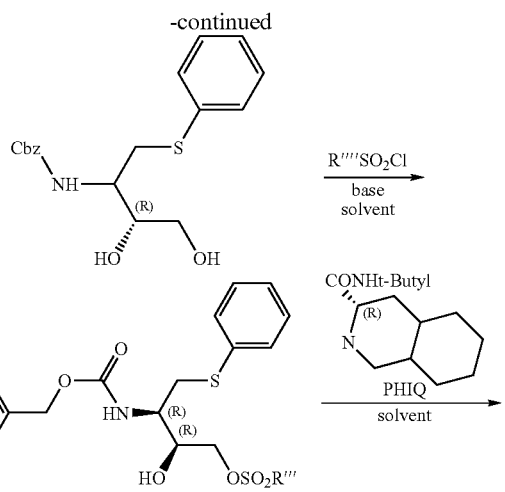

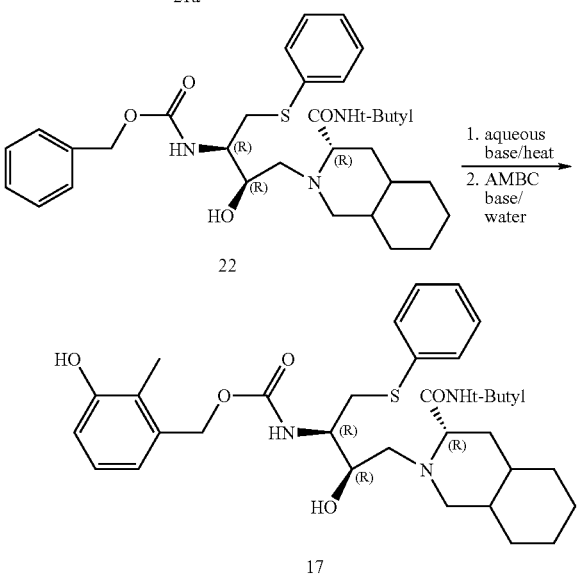

Formation of the compound of formula 22 may be achieved by treatment of a compound of formula 21a with PHIQ (3S, 4aR, 8aR, 3-N-t-butyl carboxamido-decahydroisoquinoline). Removal of the benzyloxycarbonyl nitrogen protecting group from compound 22, under conventional conditions (provided that the selected conditions do not induce racemization of the stereocenters), provides the compound of formula 16, which may be converted to nelfinavir and nelfinavir mesylate, as described above.

EXAMPLES

The structures of the compounds of the following examples were confirmed by one or more of the following: proton magnetic resonance spectroscopy, infrared spectroscopy, elemental microanalysis and melting point. Proton magnetic resonance ($^1$H NMR) spectra were determined using either a Varian UNITYplus 300 or a General Electric QE-300 spectrometer operating at a field strength of 300 megahertz (MHz). Chemical shifts are reported in parts per million (ppm, δ) downfield from an internal tetramethylsilane standard. Alternatively, $^1$H NMR spectra were referenced to residual protic solvent signals as follows:

CHCl$_3$=7.26 ppm; DMSO=2.49 ppm, C$_6$HD$_5$=7.15 ppm. Peak multiplicities are designated as follows: s, singlet; d, doublet; dd, doublet of doublets; t, triplet; q, quartet; br, broad resonance; m, multiplet. Coupling constants are given in Hertz. Infrared absorption (IR) spectra were obtained using a Perkin-Elmer 1600 series FTIR spectrometer. Elemental microanalyses were performed by Atlantic Microlab Inc., Norcross, Ga. Melting points were determined on a Mel-Temp apparatus and are uncorrected. All reactions were conducted in septum-sealed flasks under a slight positive pressure of argon unless otherwise noted. All commercial reagents were used as received from their respective suppliers with the following exceptions. Tetrahydrofuran (THF) was distilled from sodium-benzophenone ketyl prior to use. Dichloromethane (CH$_2$Cl$_2$) was distilled from calcium hydride prior to use.

Abbreviations used herein include: Et$_2$O (diethyl ether), DMF (N,N-dimethylformamide), DMSO (dimethylsulfoxide), MTBE (tert-butyl methyl ether), CH$_3$OH (methanol), EtOH (ethanol), EtOAc (ethyl acetate), DME (ethylene glycol dimethyl ether) Ac (acetyl), Me (methyl), Ph (phenyl), Tr (triphenylmethyl), Ts (tosylate), Cbz (benzyloxycarbonyl), Boc (tert-butoxycarbonyl), TFA (trifluoroacetic acid), DIEA (N,N-diisopropylethylamine), TMEDA (N,N,N',N'-tetramethylethylenediamine), AcOH (acetic acid), Ac$_2$O (acetic anhydride), NMM (4-methylmorpholine), DCC (dicyclohexyl-carbodiimide), DDQ (2,3-dichloro-5,6-dicyano-1,4-benzoquinone), DMAP (4-dimethylaminopyridine), DABCO (1,4-diazabicyclo[2.2.2]octane), DBN (1,5-diazabicyclo[4.3.0]non-5-ene), DBU (1,8-diazabicyclo[5.4.0]undec-7-ene), DMAC (N,N-dimethylacetamide), PNB (p-nitrobenzoyl), and PHIQ (3S, 4aR, 8aR, 3-N-t-butyl carboxamidodecahydroisoquinoline).

Specific examples of various compounds according to the invention may be advantageously prepared as set out in the Examples below. These examples and the compounds contained therein are not meant to limit the scope of the present invention in any way.

Example 1

Preparation of 3-phthalimido 4-thiophenylbutene 8

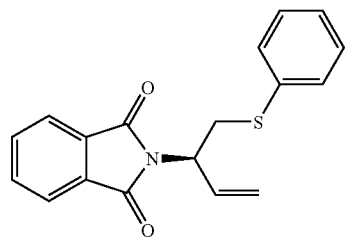

8

A solution of methanesulfonyl chloride (1.2 mol, 1.2 equiv, 137.5 g, 93 ml) in 150 ml of ethyl acetate was added to an ice-cooled (0° C.) solution of phthalimido-alcohol 6 (217.2 g, 1.0 mol, available from NSC Technologies, Mt. Prospect, Ill.) and triethylamine (1.3 mol, 1.3 equiv, 131 g and 181 ml) in 800 ml of ethyl acetate at a rate sufficient to maintain the temperature of the resulting reaction mixture below 20° C. At the end of the addition, the mixture was warmed to ambient temperature and stirred for 3 hours. HPLC analysis showed no starting material. Water (500 ml) was added and the resulting mixture was stirred for 15 minutes, after which the aqueous phase was removed. This extraction process was repeated twice using 500 ml water, followed by extraction with 500 ml brine. The bulk of the ethyl acetate was removed by distillation under vacuum at 36° C.–45° C. (pot temperature at 50° C.–70° C.) over a 2 hour period. DMF (1 L) was added and distillation of the ethyl acetate was continued under vacuum at 75° C. for 1 hour. After the resulting mixture was cooled to ambient temperature, thiophenol (2.0 mol, 2.0 equiv, 221 g, 206 ml) and diisopropyl ethylamine (2.0 mol, 2.0 equiv, 258.5 g, 350 ml) were added and the resulting mixture was heated to 65° C. (internal temperature). HPLC analysis indicated that <1% starting mesylate remained after 22 hours ($^1$H NMR analysis indicated 1–3% mesylate), $^1$H NMR of mesylate 7a: (300 MHz, CDCl$_3$,) δ 7.85 (m, 2H), 7.75 (m, 2H), 6.12 (ddd, J=7,10,18 Hz, IH), 5.40 (overlapping m, 2H), 5.10 (m, IH), 4.88 (dd, J=10, 10 Hz), 4.50 (dd, J=5, 10 Hz), 2.98 (s, 3H). The reaction mixture was cooled to ambient temperature and allowed to stand for 26 hours.

The mixture was poured into 2 L of MTBE and washed successively with 1 L portions of 1 N HCl (2×), aq. saturated NaHCO$_3$, (1×) and brine (1×). The resulting organic phase was dried with Na$_2$SO$_4$, and filtered. The filtrate was distilled at atmospheric pressure to remove the MTBE until the pot temperature reached 95° C. Distillation was stopped and the mixture was cooled to ambient temperature. The resulting solution was diluted with hexanes (1 L) then stirred. Seed crystals were added to the stirred mixture. After 10 minutes, a light orange precipitate formed. After stirring for an additional 2 hours, the solids were allowed to settle and the hexanes were decanted off. The resulting slurry was diluted with fresh hexanes (500 ml) and stirred for 30 minutes. The mixture was filtered and the light orange solid was washed with 1 L of hexanes and dried under vacuum to yield 231.9 g (75%) of 8, as an easily filterable light orange solid. The compound of formula 8 was obtained in enantiomerically pure form, as defined herein. $^1$H NMR (300 MHZ, CDCl$_3$, ) δ 7.75 (m 2H), 7.69 (m, 2H), 7.33 (d, J=7 Hz, 2H), 7.17 (t, J=7, 7 Hz, 2H), 7.09 (m, IH), 6.20, (ddd, J=7, 10, 17 Hz, IH), 5.25 (d, J=17 Hz, IH), 5.22 (d, J=10 Hz, IH), 4.90 (m, IH), 3.77 (dd, J=10, 14 Hz, IH), 3.28 (dd, J=5, 14 Hz, IH).

Example 2

Preparation of 1,2(R)-dihydroxy-3(R)phthalimido-4-(phenylthio)-butane (9) and 1,2(S)-dihydroxy-3(R)-phthalimido-4-(phenylthio)-butane (10)

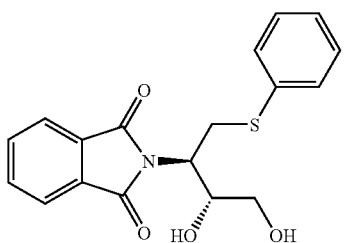

9

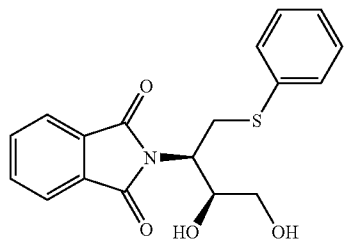

Into a 2 L Erlenmeyer flask was placed potassium ferricyanide (197.5 g, 0.60 mol, 3.0 equiv), potassium osmate (0.368 g, 0.001 mol, 0.005 equiv), sodium bicarbonate (50.4 g, 0.60 mol, 3.0 equiv), potassium carbonate (82.9 g, 0.60 mol, 3.0 equiv), methanesulfonamide (22.8 g, 0.24 mol, 1.2 equiv) and DHQD$_2$PHAL (1.55 g, 0.002 mol, 0.01 equiv). This mixture was dissolved in 900 ml of t-butanol/water (1:1 v/v) and cooled to 0° C.–5° C. Compound 8 (61.84 g, 0.20 mol, 1.0 equiv) was added as a solid in one portion. The mixture was stirred vigorously for 18 hours and quenched with 30 g of sodium bisulfite. Water (600 ml) was added and the mixture was extracted with ethyl acetate (600 ml×2 and 300 ml×2). The combined ethyl acetate extracts were washed successively with 1N NaOH (1L×1), 1N HCl (500 ml×1) and brine (1 L×1), dried with sodium sulfate and concentrated under vacuum to provide 61.7 g of a mixture of diols 9 and 10 as a gold oil, which slowly solidified on standing. The yield was approximately 90%. $^1$H NMR analysis indicated that the product was a 13:1 mixture of diol stereoisomers 9 and 10, which was used without further purification. $^1$H NMR of Compound 9: (300 MHZ, CDCl$_3$) δ 7.4–7.1 (overlapping m, 10H), 5.30 (br s, 1H), 5.09 (br s, 2H), 4.00 (m, 1H), 3.85 (m, 1H), 3.52 (overlapping m, 2H), 3.15 (overlapping m, 2H), 2.30 (br, 2H).

Example 3

Preparation of 1,2(S)-dihydroxy-3(R)-Cbz-4-(phenylthio)-butane (13) and 1,2(R)-dihydroxy-3(R)-Cbz-4-(phenylthio)-butane (14)

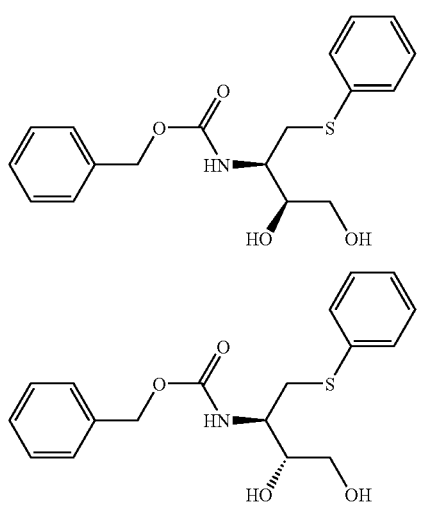

The mixture of diols 9 and 10 (6.62 g, 19.3 mmol), obtained in Example 2, was suspended in 25 ml of 40% aqueous methylamine and heated to 60° C. for 5 h. The reaction was cooled to ambient temperature and a stream of argon was bubbled through the solution for 2 hours, decreasing the volume significantly. The mixture was placed under a vacuum atmosphere (ca. 18 mm Hg) for 1 hour to remove any remaining methylamine to provide a clear brown aqueous solution. To this solution was added, successively, water (5 ml), sodium bicarbonate (2.48 g, 60 mmol) and ethyl acetate (30 ml). After cooling the resulting mixture to 5° C. (ice bath), benzyl chloroformate (3.75 g, 3.2 ml, 22 mmol) was added dropwise and the resulting mixture was stirred for 1 hour. The ethyl acetate layer was separated and washed successively with 40 ml portions of 1 N HCl, aq. saturated sodium bicarbonate and brine. The organic layer was dried with sodium sulfate, filtered and evaporated to leave 6.89 g of a mixture of Compounds 13 and 14 (as a 1:13 mixture) as a light brown oil (103%), that slowly solidified on standing.

Example 4

Preparation of 3-benzyloxycarbonylamino-4-thiophenylbutene 19

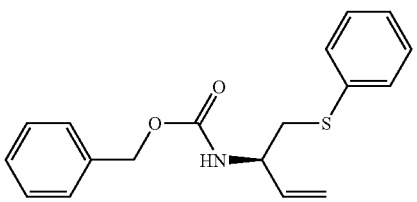

Compound 8 (50 g, 0.16M) was suspended in 250 ml of 40% aqueous methylamine, then heated to 60° (oil bath) for five hours. The resulting solution was cooled to room temperature. Remaining methylamine was removed under vacuum using a rotary evaporator. The resulting aqueous solution was extracted with ethyl acetate (2×100 ml). The ethyl acetate layers were combined and washed with 100 ml saturated NaCl, dried over sodium sulfate, filtered and concentrated under vacuum using a rotary evaporator to provide 29.11 g of the amino-butene as a yellow oil (slightly greater than theoretical yield). HPLC showed the purity to be 92%. $^1$H NMR (300 MHZ, CDCl$_3$) δ 7.35 (d, J=8 Hz, 2H), 7.27 (t, J=7, 8 Hz, 2H), 7.17 (t, J=7, 7 Hz, 1H), 5.83 (ddd, J=6, 10, 17 Hz, 1H), 5.18 (d, J=17 Hz, 1H), 5.09 (d, J=11 Hz, 1H), 3.47 (m, 1H), 3.11 (dd, J=5, 14 Hz, 1H), 2.82 (dd, J=8, 13 Hz, 1H), 1.69 (br s, 2H). This material was used without further purification.

Benzyl chloroformate (21.4 ml, 25.5 g, 0.15 mol, 1.05 equiv) was added dropwise, at room temperature, to a stirred mixture containing a solution of amino-butene (25.5 g, 0.142 mol, 1 equiv) in 120 ml of ethyl acetate and sodium bicarbonate (25.05 g, 0.298 mol, 2 equiv) in 120 ml of water. After 10 minutes, HPLC showed no starting material. After two hours of stirring, the layers were separated and the organic layer was washed with 50 ml of 0.5M citric acid, 50 ml saturated sodium bicarbonate, and 50 ml saturated sodium chloride, dried over magnesium sulfate, filtered and concentrated under vacuum using a rotary evaporator to provide 31.84 g. of 19 as a tan solid (72% yield). The solid was recrystallized from hot hexane (after a hot filtration through filter paper to remove a brown insoluble oil) to give white, needle-like crystals (24.78 g, 56% yield, in two crops). HPLC showed the purity to be 99%. $^1$H NMR (300 MHZ, CDCl$_3$) δ 7.4–7.2 (overlapping m, 10H), 5.84 (ddd, J=7, 11, 17 Hz, 1H), 5.21 (overlapping m, 2H), 5.10 (br s, 2H), 5.04 (br s, 1H), 4.45 (m, 1H), 3.15 (m, 2H).

Example 5

Preparation of 3-benzyloxycarbonylamino-4-thiophenylbutane diols 13 and 14

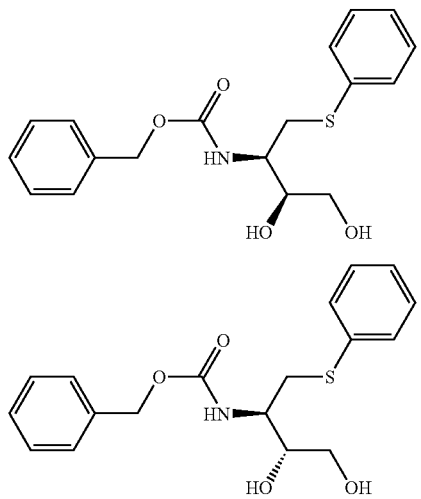

Compound 19 (1 g, 0.003 mol, 1.0 equiv) was added as a solid, in one portion, to a 3-neck roundbottom flask containing a 0° C.–5° C. solution of potassium ferricyanide (2.96 g, 0.009 mol, 3 equiv), potassium osmate (0.005 g, 0.000015 mol, 0.005 equiv), sodium bicarbonate (0.76 g, 0.009 mol, 3 equiv), potassium carbonate (1.24 g, 0.009 mol, 3 equiv), methanesulfonamide (0.28 g, 0.003 mol, 1 equiv) and (DHQ)$_2$PYR (0.026 g, 0.00003 mol, 0.01 equiv) in 15 ml of t-butanol/water (1:1 v/v). The resulting mixture was stirred for 12 hrs at 0° C.–5° C., then at room temperature for eighteen hours. The solid product was then filtered, washed with t-butanol/water (1:1 v/v) and dried to give 0.9 g of a white solid (86% yield). The HPLC showed a ratio of 4:1 of diols 13 and 14. This product mixture was recrystallized from ethylacetate/hexane (3:1 v/v) to give 0.18 g of 13 as a white crystalline solid. HPLC showed 97% pure 13. $^1$H NMR (300 MHZ, CDCl$_3$) δ 7.4–7.2 (overlapping m, 10H), 5.2 (d, 1H), 5.1 (s, 1H), 3.9 (br m, 1H), 3.7 (m, 2H), 3.5 (m, 1H), 3.3 (m, 2H), 3.1 (m, 1H) 2.6 (d, 1H).

Example 6

Preparation of 3-benzyloxycarbonylamino-4-phenylthio-1-buteneoxide 15

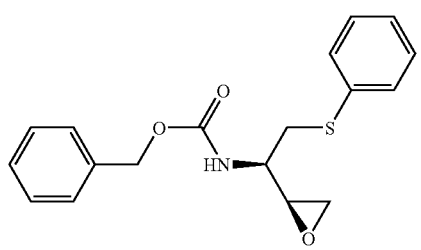

p-Nitrobenzoyl chloride (20.8 g, 0.112 mol) was added at 3–10° C. to a 0° C. to 5° C. solution of (2R, 3R)-3-benzyloxycarbonylamino-4-phenylthio-1,2-butanediol 14 (39.0 g) and triethylamine (39.1 ml, 0.280 mol) in tetrahydrofuran (300 ml). The resulting mixture was stirred for one hour with ice-cooling. Methanesulfonyl chloride (10.4 ml, 0.135 mol) was added dropwise at 2–12° C. and the mixture was stirred with ice-cooling for one hour. Any insoluble matter was filtered off and washed with ethyl acetate. The filtrate and the washing were combined and concentrated under vacuum. The resulting residue was dissolved in ethyl acetate (300 ml) and washed successively with water (50 ml), a 0.5 M aqueous citric acid solution (50 ml), a saturated aqueous solution of sodium hydrogencarbonate (50 ml) and saturated brine (50 ml), dried over magnesium sulfate and concentrated under vacuum. The resulting residue was recrystallized from toluene (400 ml)/diisopropyl ether (300 ml) to give (2R, 3R)-3-benzyloxycarbonylamino-4-phenylthio-2-methanesulfonyloxy-1-(4-nitrobenzyloxy)butane (38.6 g, 51% yield from (2R, 3R)-3-benzyloxycarbonylamino-4-phenylthio-1,2-butanediol 14) as colorless crystals. $^1$H NMR (CDCl$_3$, 300 MHz) δ 8.5–8.0 (m, 4H), 7.5–7.2 (m, 10H), 5.44 (ddd, J=6.9, 5.1, 2.3 Hz, 1H), 5.11 (s, 2H), 5.09 (brd d, 1H), 4.57 (dd, J=12.0, 6.9 Hz, 1H), 4.50 (dd, J=12.0, 5.1 Hz, 1H), 4.21 (m, 1H), 3.25 (dd, J=14.0, 6.2 Hz, 1H), 3.05 (s, 3H), 3.05 (dd, J=14.0, 8.2 Hz, 1H) IR (KBr): 3347, 1725, 1699, 1531, 1514, 1349, 1283, 1172, 1109, 1028, 925 cm$^{-1}$, $[\alpha]_D^{25}$: −14.0° (c1.01,CHCl$_3$); Elemental Analysis (C$_{26}$H$_{26}$N$_2$O$_9$S$_2$): Calculated: C, 54.35; H, 4.56; N, 4.88; Found: C, 54.49; H, 4.19; N, 4.75.

An aqueous solution of 2N potassium hydroxide solution (28.7 ml, 57.4 mmol) was added to a stirred, room temperature solution of (2R, 3R)-3-benzyloxycarbonylamino-4-phenylthio-2-methanesulfonyl-oxy-1-(4-nitrobenzoyloyloxy) butane (15.0 g, 26.1 mol) in 1,4-dioxane (120 ml). The resulting mixture was stirred for one hour at room temperature. Toluene (200 ml) was added and the resulting mixture was washed successively with water (200 ml), a saturated aqueous solution of sodium hydrogencarbonate (200 ml) and saturated brine (100 ml), dried over magnesium sulfate and concentrated under vacuum to give (2S, 3R)-3-benzyloxycarbonylamino-4-phenylthio-1-buteneoxide 15, 8.43 g, (98% yield) as a colorless oil. This material was used without further purification. $^1$H NMR (CDCl$_3$, 300 MHz) δ 7.5–7.1 (m, 10H), 5.2–5.0 (m, 3H), 3.70 (m, 1H), 3.22 (d, J=5.6 Hz, 2H), 2.99 (m, 1H), 2.9–2.6 (m, 2H) IR (KBr): 3302, 1694, 1538, 1323, 1256, 1100, 1028, 1006, 882 cm$^{-1}$ $[\alpha]_D^{25}$: −26.2 δ (c1.01, CHCl$_3$); Elemental Analysis (C$_{18}$H$_{19}$NO$_3$S): Calculated: C, 65.63; H, 5.81; N, 4.25, Found: C, 65.36; H, 5.85; N, 4.33.

Example 7

Preparation of (3S, 4aS, 8aS)-2-((2R, 3R)-3-amino-2-hydroxy-4-phenylthiobutyl)-decahydroisoquinaline-3-carboxylic acid t-butylamide 16

16

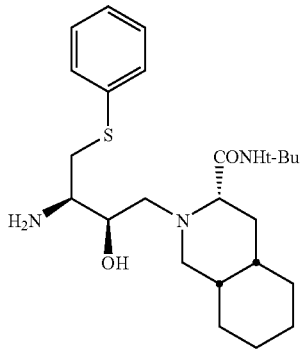

A solution of (2S, 3R)-3-benzyloxycarbonylamino-4-phenylthio-1-buteneoxide 15 (8.43 g) and (3S, 4aS, 8aS)-decahydroisoquinoline-3-carboxylic acid t-butylamide (4.98 g, 20.9 mmol) in isopropyl alcohol (70 ml) was heated at 70–75° C. for 5 hours. An aqueous solution of 2N potassium hydroxide (52.3 ml, 104.5 mmol) was added and heating was continued at 70–75° C. for 15 hours. After cooling to room temperature, toluene (120 ml) was added and the mixture was washed with water (120 ml) and 1N hydrochloric acid (80 ml×1, 40 ml×1). The aqueous extracts were combined and washed with toluene (100 ml×3). The pH of the aqueous extracts was adjusted to pH 12 using a aqueous solution of 5N potassium hydroxide, then extracted with toluene (120 ml). The combined organic layers were washed with saturated brine, dried over magnesium sulfate and concentrated under vacuum to give (3S, 4aS, 8aS)-2-((2R, 3R)-3-amino-2-hydroxy-4-phenylthiobutyl)-decahydroisoquinaline-3-carboxylic acid t-butylamide 16, 9.39 g, yield 85%, as a colorless oil. $^1$H NMR (CDCl$_3$, 300 MHz) δ 7.5–7.1 (m, 5H), 6.05 (brd s, 1H), 3.68 (m, 1H), 3.37 (dd, J=13.0, 2.8 Hz, 1H), 3.02–2.88 (m, 2H), 2.83 (dd, J=13.0, 9.8 Hz, 1H), 2.64 (dd, J=13.2, 5.1 Hz, 1H), 2.60 (dd, J=8.0.3.7 Hz, 1H), 2.30 (dd, J=13.2, 6.6 Hz, 1H), 2.27 (dd, J=11.8, 3.3 Hz, 1H), 1.32 (s.9HI), 2.0–1.0 (m, 12H)

Example 8

Preparation of (3S, 4aS, 8aS)-2-[(2R, 3R)-2-hydroxy-3-(3-hydroxy-2-methylbenzoylamino)-4-phenylthiobutyl]decahydroisoquinoline-3-carboxylic acid t-butylamide 17

17

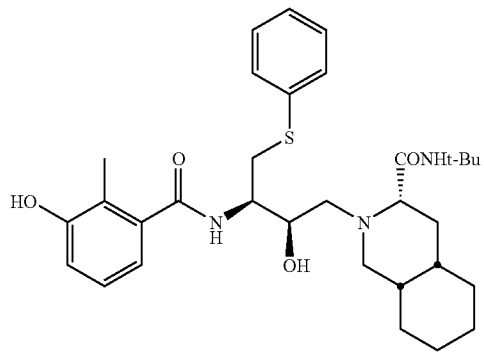

A solution of 3-acetoxy-2-methylbenzoyl chloride (4.37 g, 20.6 mmol) in ethyl acetate (40 ml) was dropwise added to a stirred suspension (3S, 4aS, 8aS)-2-((2R, 3R)-3-amino-2-hydroxy-4-phenylthiobutyl)-decahydroisoquinoline-3-carboxylic acid t-butylamide 16 (9.1 g, 21 mmol) and sodium hydrogencarbonate (4.55 g, 54.2 mmol) in a mixture of water (40 ml) and ethyl acetate (40 ml), with ice-cooling. The mixture was stirred for an additional hour with ice-cooling. Water (20 ml) was added and the organic layer was separated and washed with a saturated aqueous solution (20 ml) of sodium hydrogencarbonate, dried over magnesium sulfate and concentrated under vacuum to give (3S, 4aS, 8aS)-2-[(2R, 3R)-3-(3-acetoxy-2-methylbenzoylamino)-2-hydroxy-4-phenylthiobutyl]-decahydroisoquinaline-3-carboxylic acid t-butylamide (12.7 g, yield 96%) as colorless and amorphous. $^1$H NMR (CDCl$_3$, 300 MHz) δ 7.5–7.1 (m, 8H), 7.1–7.0 (m, 1H), 5.51 (brd s, 1H), 4.48 (m, 1H), 4.07 (m, 1H), 3.81 (dd, J=13.7, 9.2 Hz, 1H), 3.41 (dd, J=13.7, 4.7 Hz, 1H), 2.91 (dd, J=11.7, 2.0Hz, 1H), 2.56 (dd, J=12.9, 9.1 Hz, 1H), 2.44 (m, 1H), 2.32 (s, 3H), 2.27 (s, 3H), 2.3–2.1 (m, 2H), 1.99 (m, 1H), 1.9–1.1 (m, 11H), 1.07 (s, 9H)

Aqueous ammonia (28%, 24 ml) was added to a solution of (3S, 4aS, 8aS)-2-[(2R, 3R)-3-(3-acetoxy-2-methyl-benzoylamino)-2-hydroxy-4-phenylthiobutyl]-decahydroisoquinoline-3-carboxylic acid t-butylamide (12.7 g) in methanol (96 ml). The resulting mixture was stirred for 1.5 hours at room temperature. The resulting precipitate was collected by filtration and washed with a mixed solution of methanol (75 ml)/water (25 ml). The residue was dried at 50° C. under vacuum to give (3S, 4aS, 8aS)-2-[(2R, 3R)-2-hydroxy-3-(3-hydroxy-2-methylbenzoylamino)-4-phenylthiobutyl]decahydroisoquinoline-3-carboxylic acid t-butylamide 17, 8.00 g, as colorless crystals (54% yield from (2R, 3R-benzyloxycarbonylamino-4-phenylthio-2-methanesulfonyloxy-1-(4-nitrobenzoyloxy) butane). $^1$H NMR (CD$_3$OD, 300 MHz) δ 7.49 (m, 2H), 7.27 (m, 2H), 7.17 (m, 1H), 7.01 (m, 1H), 6.90 (m, 1H), 6.79 (m, 1H), 4.43 (M, 1H), 4.06 (m, 1H), 3.54 (dd, J=10.1, 3.5 Hz, 1H), 3.37 (m, 1H), 3.04 (dd, J=8.7, 1.7 Hz, 1H), 2.60 (m, 2H), 2.24 (s, 3H), 2.17 (m, 2H), 2.01 (M, 1H), 1.9–1.1 (m, 11H), 1.17 (s, 9H).

The examples and preparations provided above further illustrate and exemplify the compounds of the present invention and methods of preparing such compounds. It is to be understood that the scope of the present invention is not limited in any way by the scope of the following examples and preparations.

The invention claimed is:

1. A compound selected from the group consisting of:

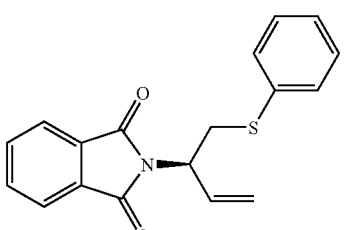

and

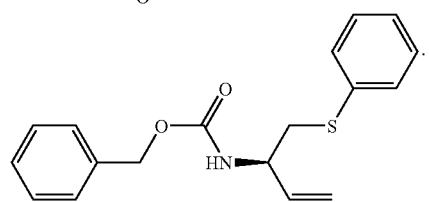

2. A compound having the formula
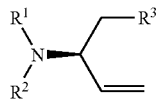
wherein $R^1$ and $R^2$ together with the nitrogen to which they are bound form a phthalimido, succinimido or diformyl moiety; and
$R^3$ is thioalkyl or thioaryl.
* * * * *